United States Patent
Hürlimann et al.

(10) Patent No.: US 9,658,358 B2
(45) Date of Patent: May 23, 2017

(54) REFOCUSING PULSES AND EXCITATION PULSES FOR NMR LOGGING

(75) Inventors: Martin D. Hürlimann, Newton, MA (US); Soumyajit Mandal, Cambridge, MA (US); Van Mai Do, Cambridge, MA (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1430 days.

(21) Appl. No.: 13/338,083

(22) Filed: Dec. 27, 2011

(65) Prior Publication Data
US 2013/0162247 A1    Jun. 27, 2013

(51) Int. Cl.
| | |
|---|---|
| *G01V 3/14* | (2006.01) |
| *G01V 3/32* | (2006.01) |
| *G01N 24/08* | (2006.01) |
| *G01R 33/561* | (2006.01) |
| *G01R 33/38* | (2006.01) |
| *G01R 33/44* | (2006.01) |

(52) U.S. Cl.
CPC ............ *G01V 3/32* (2013.01); *G01N 24/081* (2013.01); *G01R 33/5617* (2013.01); *G01R 33/3808* (2013.01); *G01R 33/445* (2013.01)

(58) Field of Classification Search
CPC .. G01N 24/081; G01N 24/084; G01N 24/087; G01V 3/32; G01V 3/14; G01R 33/448; G01R 33/5617; G01R 33/445; G01R 33/3808; G01R 33/54; G01R 33/543; G01R 33/28

USPC .................................................. 324/300–322
See application file for complete search history.

(56) References Cited

U.S. PATENT DOCUMENTS

| | | | |
|---|---|---|---|
| 5,023,551 A | 6/1991 | Kleinberg et al. | |
| 5,055,787 A | 10/1991 | Kleinberg et al. | |
| 5,055,788 A | 10/1991 | Kleinberg et al. | |
| 6,462,542 B1 | 10/2002 | Venkataramanan et al. | |
| 6,597,171 B2* | 7/2003 | Hurlimann | G01V 3/32 |
| | | | 324/300 |
| 2003/0052677 A1* | 3/2003 | Pines et al. | 324/307 |

(Continued)

OTHER PUBLICATIONS

Definition of Refocusing, Magnetic Resonance Technology Information Portal, <http://www.mr-tip.com/serv1.php?type=db1&dbs=Refocusing>, May 13, 2015.*

(Continued)

*Primary Examiner* — Melissa Koval
*Assistant Examiner* — Rishi Patel

(57) ABSTRACT

Illustrative embodiments are directed to applying a nuclear magnetic resonance sequence to a substance within an inhomogeneous static magnetic field. Various embodiments include applying a series of refocusing pulses to the substance, each refocusing pulse in the series of refocusing pulses having at least two segments, and a total pulse duration less than or equal to approximately 1.414 times $T_{180}$. Various embodiments can further include applying an excitation pulse to the substance in the inhomogeneous static magnetic field, where the excitation pulse generates an initial magnetization that is aligned with a refocusing axis produced by a refocusing cycle that is performed after the excitation pulse.

18 Claims, 25 Drawing Sheets

(56) References Cited

U.S. PATENT DOCUMENTS

| | | | |
|---|---|---|---|
| 2004/0189296 A1* | 9/2004 | Sun et al. .................... | 324/306 |
| 2005/0248342 A1* | 11/2005 | Rottengatter et al. ........ | 324/303 |
| 2005/0275401 A1* | 12/2005 | Blanz et al. .................. | 324/303 |
| 2008/0024128 A1* | 1/2008 | Song .................... | G01N 24/081 |
| | | | 324/307 |
| 2009/0033326 A1* | 2/2009 | Szyperski et al. ............ | 324/307 |
| 2009/0230958 A1* | 9/2009 | Balchandani et al. ........ | 324/309 |

OTHER PUBLICATIONS

Borneman et al., Application of optimal control to CPMG refocusing pulse design; Journal of Magnetic Resonance 207, (2010); pp. 220-233.

Carr et al., Effects of Diffusion on Free Precession in Nuclear Magnetic Resonance Experiments; Physical Review 94:3; (1954) 13 pages.

Encyclopedia of Nuclear Magnetic Resonance, vol. 2; Composite Pulses, (1996), pp. 1396-1411.

Hopper et al., Low Frequency NMR with a non-resonant circuit; Journal of Magnetic Resonance 210 (2011) pp. 69-74.

Hurlimann et al., Spin Dynamics of Carr-Purcell-Meiboom-gill-like Sequences in Grossly Inhomogeneous B0 and B1 Fields and Application to NMR Well Logging; Journal of Magnetic Resonance 143, (2000) 120-135.

M.D. Hurlimann; Carr-Purcell Sequences with Composite Pulses; Journal of Magnetic Resonance 152, (2001) pp. 109-123.

M.D. Hurlimann; Diffusion and Relaxation Effects in General Stray Field NMR Experiments; Journal of Magnetic Resonance 148, (2001) pp. 367-378.

Meiboom et al., Modified Spin-Echo Method for Measuring Nuclear Relaxation Times; The Review of Scientific Instruments, 29:8, (1958) pp. 688-691.

Poon et al., 180° Refocusing Pulses Which are Insensitive to Static and Radiofrequency Field Inhomogeneity; Journal of Magnetic Resonance 99, (1992) pp. 45-55.

Poon et al., Robust Refocusing Pulses of Limited Power; Journal of Magnetic Resonance, Series A 116 (1995) pp. 161-180.

C. P. Slichter; Principles of Magnetic Resonance, Third Enlarged and Updated Edition, pp. 39-45.

* cited by examiner

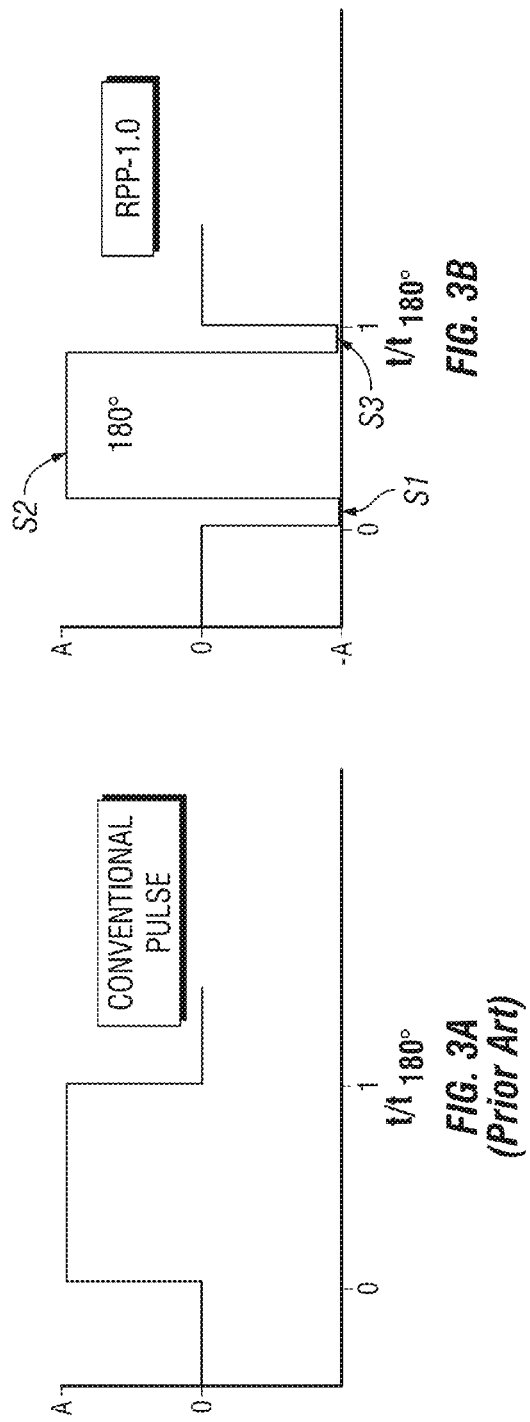
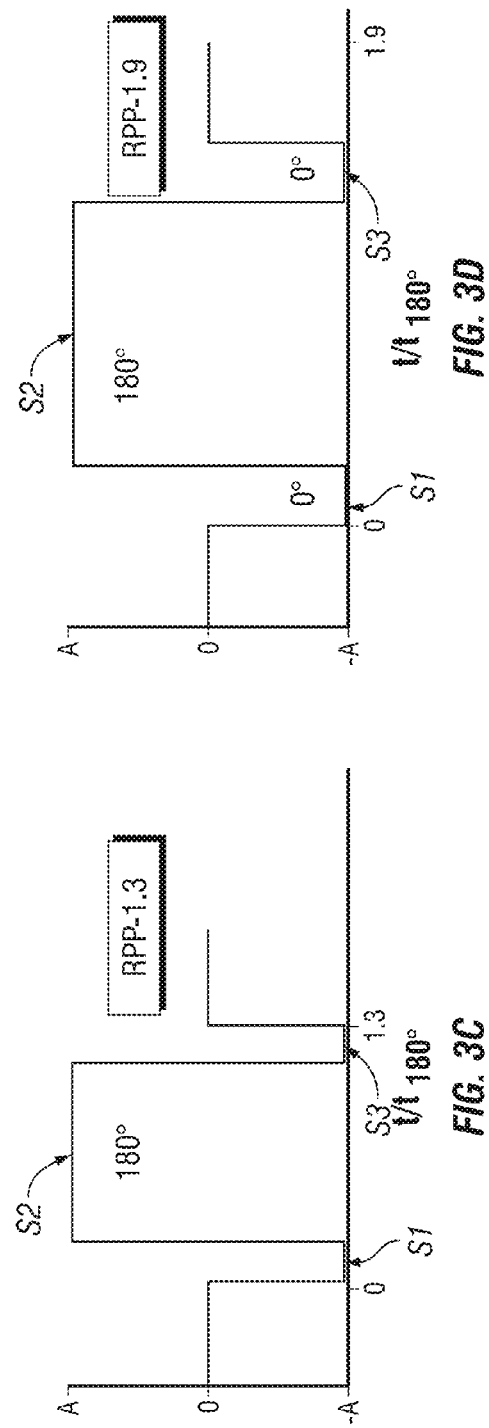
FIG. 3A (Prior Art)
FIG. 3B
FIG. 3C
FIG. 3D (Conventional Pulse)

(Conventional Pulse)

| TABLE 1 | | |
|---|---|---|
| PULSE NAME | PERFECT 90° PULSE | PERFECT ALIGNMENT WITH THE AXIS |
| CONVENTIONAL PULSE | 1.00 | 1.72 |
| RPP-1.0 | 1.80 | 3.31 |
| RPP-1.3 | 2.05 | 3.32 |
| RPP-1.9 | 2.19 | 3.25 |

TABLE 2 - EXCITATION PULSE A

| NOS. | 1-19 | 20-38 | 39-57 | 58-76 | 77-95 | 96-100 |
|---|---|---|---|---|---|---|
| PHASE (°) | 88.0433 | 355.7718 | 118.9414 | 264.7512 | 93.8024 | 159.5545 |
| | 103.811 | 305.2195 | 138.2413 | 269.9799 | 359.2212 | 231.3824 |
| | 79.4558 | 293.4935 | 278.7882 | 354.7073 | 249.35 | 181.3576 |
| | 276.3981 | 65.5664 | 316.6545 | 130.5318 | 130.6543 | 272.0567 |
| | 18.1564 | 40.1902 | 358.1128 | 224.8874 | 102.8841 | 233.9551 |
| | 32.7776 | 131.8584 | 359.1525 | 316.1575 | 329.1469 | |
| | 70.6377 | 234.0008 | 309.2609 | 237.4761 | 197.0726 | |
| | 205.7088 | 233.2455 | 127.9629 | 94.4609 | 120.1079 | |
| | 259.0698 | 111.2553 | 68.5675 | 29.6069 | 66.9039 | |
| | 40.1385 | 101.3571 | 59.7753 | 247.1955 | 314.3425 | |
| | 9.3316 | 265.3377 | 175.8213 | 277.1054 | 28.1789 | |
| | 325.1111 | 108.6119 | 63.0658 | 302.6697 | 221.9813 | |
| | 211.8101 | 240.801 | 81.046 | 201.3028 | 237.3862 | |
| | 229.3037 | 253.1032 | 262.5219 | 234.0294 | 270.7901 | |
| | 90.6834 | 166.4233 | 271.4495 | 327.7967 | 281.6644 | |
| | 198.242 | 145.1778 | 194.8918 | 81.9899 | 117.0946 | |
| | 174.7467 | 153.2779 | 253.2771 | 98.3932 | 189.1313 | |
| | 157.2696 | 110.7538 | 198.7417 | 124.1686 | 139.8115 | |
| | 103.444 | 196.8858 | 318.9022 | 131.5794 | 234.5609 | |

TABLE 3 - EXCITATION PULSE B

| NOS. PHASE (°) | 1-19 | 20-38 | 39-57 | 58-76 | 77-95 | 96-114 | 115-133 | 134-152 | 153-162 |
|---|---|---|---|---|---|---|---|---|---|
| | 307.5255 | 316.797 | 209.7969 | 153.7741 | 74.8456 | 183.7301 | 289.0839 | 200.6632 | 267.2073 |
| | 350.5473 | 32.2231 | 344.642 | 125.1915 | 192.349 | 329.0704 | 342.0074 | 80.3958 | 123.9952 |
| | 292.8902 | 321.6394 | 44.0603 | 124.1572 | 8.8056 | 129.3046 | 305.9009 | 84.5584 | 222.8027 |
| | 241.5462 | 178.197 | 101.7274 | 210.8063 | 238.3936 | 146.8872 | 251.8306 | 318.5326 | 256.7486 |
| | 247.1899 | 185.8269 | 22.3324 | 164.57 | 225.1829 | 80.4554 | 310.0091 | 258.9363 | 112.6289 |
| | 222.7779 | 272.228 | 36.8887 | 213.8283 | 165.2841 | 23.5662 | 33.215 | 219.3329 | 141.9325 |
| | 166.8651 | 3.795 | 2.8945 | 320.6793 | 49.1517 | 114.8476 | 56.8027 | 136.1085 | 176.093 |
| | 228.8702 | 232.0079 | 315.783 | 163.3997 | 151.0655 | 100.9056 | 63.5178 | 299.7526 | 307.6583 |
| | 41.5186 | 125.1098 | 316.8393 | 258.4591 | 16.3334 | 239.0242 | 204.0908 | 121.6114 | 237.0281 |
| | 164.1292 | 222.2092 | 112.9033 | 194.6605 | 327.4217 | 321.6639 | 159.429 | 45.3297 | 123.2927 |
| | 226.1992 | 130.3625 | 247.7204 | 186.5574 | 272.3143 | 147.8621 | 351.1048 | 306.2315 | |
| | 310.6724 | 171.1906 | 291.7828 | 266.2685 | 201.8668 | 250.6618 | 279.4556 | 3.2755 | |
| | 80.861 | 94.6032 | 93.916 | 12.1972 | 179.6762 | 310.7862 | 191.4156 | 198.7941 | |
| | 168.573 | 63.9668 | 106.7549 | 2.3094 | 304.6529 | 40.4908 | 258.0524 | 96.1211 | |
| | 206.5005 | 84.394 | 32.8918 | 267.5152 | 245.3261 | 134.3728 | 317.475 | 235.2752 | |
| | 261.2175 | 274.7324 | 120.0265 | 131.6752 | 232.4122 | 221.8904 | 280.6974 | 139.4716 | |
| | 96.0151 | 43.9201 | 97.0193 | 217.0037 | 201.7842 | 197.0893 | 301.4763 | 143.7288 | |
| | 356.1522 | 21.9306 | 78.9312 | 244.4164 | 203.2664 | 80.6927 | 222.8005 | 224.2227 | |
| | 220.1418 | 120.9786 | 134.2826 | 154.4246 | 210.1182 | 24.6702 | 196.3396 | 229.1317 | |

TABLE 4 - EXCITATION PULSE C

| NOS. PHASE(°) | 1-19 | 20-38 | 39-57 | 58-76 | 77-95 | 96-114 | 115-133 | 134-152 | 153-171 | 172-190 | 191-202 |
|---|---|---|---|---|---|---|---|---|---|---|---|
| | 130.6486 | 5.8579 | 70.8234 | 256.9916 | 270.3941 | 285.3153 | 234.0615 | 27.4294 | 178.1 | 105.2701 | 216.6341 |
| | 136.3545 | 140.3321 | 51.7904 | 165.107 | 178.6109 | 275.1426 | 265.355 | 187.2216 | 77.9499 | 114.1027 | 82.4257 |
| | 246.7286 | 323.3482 | 357.6709 | 125.0242 | 113.8221 | 160.408 | 173.2009 | 78.838 | 83.0129 | 301.6128 | 72.1975 |
| | 165.3561 | 26.6059 | 306.2436 | 277.853 | 260.2301 | 202.2293 | 206.3708 | 220.9139 | 337.4088 | 297.8917 | 226.9025 |
| | 280.1394 | 308.9957 | 44.8572 | 54.443 | 302.0036 | 140.1257 | 268.2523 | 12.6436 | 108.4887 | 290.4162 | 14.4732 |
| | 209.7881 | 241.6093 | 139.9165 | 73.4608 | 4.2256 | 69.3507 | 5.7408 | 151.7682 | 91.9694 | 336.1144 | 210.8621 |
| | 224.6459 | 129.7156 | 115.9195 | 35.0536 | 196.8617 | 84.266 | 313.4486 | 229.1446 | 58.0231 | 152.1214 | 222.2872 |
| | 140.321 | 40.9253 | 246.7748 | 82.4138 | 64.2999 | 92.2415 | 8.3578 | 199.6661 | 57.865 | 206.2584 | 233.3404 |
| | 189.3244 | 268.8701 | 245.3529 | 147.9036 | 193.7168 | 316.6288 | 75.2323 | 204.6254 | 179.7298 | 151.5527 | 149.7344 |
| | 281.9536 | 175.9168 | 138.869 | 85.7735 | 251.57 | 287.6793 | 104.8206 | 164.2788 | 308.9969 | 104.1345 | 71.0288 |
| | 238.9759 | 168.9419 | 268.0354 | 53.4874 | 108.893 | 52.1216 | 195.5081 | 176.7478 | 212.2647 | 160.3151 | 9.6046 |
| | 208.8584 | 257.2829 | 231.3655 | 269.1439 | 302.0167 | 115.3659 | 254.6754 | 344.1393 | 211.0624 | 300.8966 | 158.2292 |
| | 143.4399 | 235.9081 | 64.0419 | 64.7179 | 247.3541 | 101.4464 | 163.1278 | 197.9296 | 22.8224 | 234.7914 | |
| | 196.9418 | 83.8126 | 123.5806 | 120.3835 | 208.9872 | 83.6143 | 55.665 | 129.5588 | 41.5713 | 231.5428 | |
| | 84.7726 | 1.7197 | 54.5181 | 82.6741 | 235.1296 | 103.2726 | 139.0094 | 249.6858 | 224.584 | 183.2767 | |
| | 46.0874 | 51.9804 | 84.6158 | 67.5661 | 240.1026 | 200.9984 | 137.0894 | 244.812 | 172.4624 | 235.3077 | |
| | 282.149 | 153.7452 | 50.9384 | 147.7675 | 271.3675 | 243.7317 | 163.4886 | 209.2436 | 72.0084 | 149.2767 | |
| | 288.3951 | 84.971 | 213.8703 | 121.8984 | 278.1241 | 90.6784 | 198.0855 | 24.7619 | 43.9204 | 106.6166 | |
| | 14.5595 | 215.2474 | 13.247 | 39.2846 | 301.7688 | 229.1304 | 266.1526 | 168.029 | 42.5559 | 185.3418 | |

FIG. 14

TABLE 5 - EXCITATION PULSE D

| NOS. PHASE (°) | 1-19 | 20-38 | 39-57 | 58-76 | 77-95 | 96-114 | 115-133 | 134-152 | 153-156 |
|---|---|---|---|---|---|---|---|---|---|
| | 53.7926 | 308.7682 | 345.3706 | 335.9885 | 321.3751 | 137.1209 | 23.9691 | 45.8488 | 340.2491 |
| | 90.497 | 357.8264 | 187.5777 | 218.518 | 334.8644 | 3.0538 | 38.2832 | 215.2915 | 263.4012 |
| | 155.7887 | 272.3872 | 261.3245 | 357.9713 | 218.0926 | 218.8954 | 155.2947 | 191.4446 | 260.6354 |
| | 130.9887 | 234.5611 | 246.8266 | 8.2703 | 44.2574 | 244.9866 | 279.7938 | 99.6892 | 186.4033 |
| | 288.8853 | 285.6404 | 280.4222 | 250.2897 | 86.0076 | 145.5561 | 301.2864 | 236.5543 | |
| | 198.2282 | 167.5831 | 11.8006 | 76.5211 | 134.4305 | 227.4417 | 122.0673 | 337.0812 | |
| | 148.3741 | 126.6816 | 91.3884 | 270.0948 | 60.582 | 4.3316 | 213.2428 | 251.7858 | |
| | 232.6068 | 143.8243 | 258.4517 | 24.4033 | 202.2181 | 122.1141 | 116.2437 | 106.4218 | |
| | 182.1143 | 213.1605 | 275.6595 | 278.7376 | 209.8629 | 69.3217 | 142.8734 | 250.9525 | |
| | 265.6159 | 56.0786 | 252.6615 | 98.7167 | 205.0772 | 354.3082 | 131.309 | 259.1106 | |
| | 148.0611 | 279.745 | 242.2749 | 198.3846 | 209.4726 | 184.9195 | 240.3971 | 165.2504 | |
| | 102.7562 | 141.3437 | 29.1449 | 53.7993 | 198.9153 | 295.2492 | 158.5921 | 198.3783 | |
| | 75.7578 | 108.1845 | 103.1291 | 358.2802 | 178.0144 | 348.2881 | 114.682 | 161.6576 | |
| | 95.8261 | 248.0944 | 91.8247 | 143.1185 | 82.1419 | 258.3887 | 350.0055 | 87.5754 | |
| | 316.4344 | 221.056 | 161.0623 | 266.2437 | 357.9547 | 311.1233 | 354.3523 | 291.0206 | |
| | 157.6428 | 186.5734 | 157.4431 | 274.7253 | 287.7277 | 272.695 | 239.9419 | 266.3695 | |
| | 200.174 | 247.2108 | 88.7567 | 178.1461 | 345.7024 | 1.959 | 241.6007 | 169.3954 | |
| | 282.7743 | 218.833 | 72.6743 | 172.9948 | 62.6357 | 257.2652 | 169.8639 | 208.5156 | |
| | 302.6995 | 305.9795 | 343.4343 | 330.9261 | 165.7995 | 274.5418 | 153.9527 | 67.0504 | |

*FIG. 15*

TABLE 6 - EXCITATION PULSE E

| NOS. PHASE (°) | 1-19 | 20-38 | 39-57 | 58-76 | 77-95 | 96-114 | 115-133 | 134-144 |
|---|---|---|---|---|---|---|---|---|
| | 115.8093 | 240.8392 | 257.7674 | 190.3944 | 134.1965 | 32.007 | 186.4062 | 223.8183 |
| | 136.9868 | 120.0386 | 283.9594 | 320.5071 | 145.0308 | 133.8601 | 67.5389 | 233.1483 |
| | 136.8226 | 90.8624 | 61.5976 | 333.8093 | 207.7208 | 118.2338 | 256.6804 | 112.9753 |
| | 208.572 | 3.3222 | 192.8279 | 235.0694 | 185.5087 | 357.8713 | 186.8206 | 223.8132 |
| | 82.9752 | 228.1553 | 238.1247 | 132.688 | 90.3393 | 305.8078 | 89.4436 | 43.844 |
| | 187.3393 | 66.1774 | 277.5296 | 78.7332 | 264.6025 | 5.7386 | 118.2971 | 287.1773 |
| | 244.0005 | 205.9703 | 159.0432 | 101.5413 | 167.2083 | 335.6376 | 165.979 | 129.1772 |
| | 126.5787 | 304.3345 | 91.9154 | 260.2715 | 252.0746 | 289.4477 | 221.8252 | 161.7876 |
| | 18.0354 | 286.7491 | 77.0496 | 244.1948 | 156.5428 | 324.0879 | 273.2396 | 165.6868 |
| | 304.5938 | 217.5552 | 48.4685 | 188.0098 | 211.0854 | 223.2113 | 185.7603 | 251.0365 |
| | 8.6635 | 240.7272 | 40.8688 | 282.3198 | 212.3967 | 242.4353 | 148.5291 | 309.7358 |
| | 299.5912 | 264.6064 | 95.3367 | 305.1568 | 294.6297 | 2.0525 | 335.8328 | |
| | 266.3985 | 160.577 | 340.4442 | 358.3651 | 288.196 | 2.6523 | 303.4329 | |
| | 123.9636 | 19.6065 | 358.7495 | 321.0903 | 345.2587 | 138.3656 | 339.2791 | |
| | 160.4344 | 244.3027 | 108.5346 | 275.3189 | 145.9937 | 201.0065 | 125.0779 | |
| | 229.3303 | 227.7736 | 274.7396 | 110.9669 | 202.537 | 314.7788 | 165.0203 | |
| | 271.6198 | 292.9406 | 100.0476 | 78.9558 | 254.122 | 286.507 | 179.9373 | |
| | 177.4076 | 300.167 | 2.067 | 82.1551 | 181.2692 | 184.7163 | 267.7333 | |
| | 153.1988 | 218.8466 | 8.5899 | 66.0037 | 64.0097 | 178.8265 | 253.3801 | |

FIG. 16

TABLE 7 - EXCITATION PULSE F

| NOS. | 1-19 | 20-38 | 39-57 | 58-76 | 77-95 | 96-114 | 115-132 |
|---|---|---|---|---|---|---|---|
| PHASE (°) | 1.6734 | 155.3265 | 102.7682 | 81.014 | 91.8813 | 253.8349 | 160.0515 |
| | 17.476 | 78.3258 | 151.4181 | 299.2655 | 206.5149 | 256.5503 | 248.4827 |
| | 48.7448 | 218.3593 | 285.586 | 244.2303 | 227.7695 | 123.7273 | 281.6498 |
| | 68.8099 | 211.6231 | 283.5356 | 145.4953 | 309.7419 | 215.5024 | 261.8933 |
| | 67.0055 | 232.7709 | 81.4267 | 264.9752 | 35.978 | 114.8894 | 1.4451 |
| | 3.8545 | 355.1969 | 280.0713 | 167.254 | 200.526 | 175.0109 | 189.6624 |
| | 156.6452 | 201.0007 | 58.8144 | 108.3001 | 336.0767 | 148.8054 | 164.063 |
| | 247.8278 | 2.6402 | 193.0224 | 256.7541 | 350.3591 | 154.1287 | 127.7986 |
| | 218.8358 | 169.8242 | 291.3033 | 197.8548 | 0.6522 | 76.3583 | 197.6827 |
| | 202.342 | 178.2763 | 334.7238 | 145.5036 | 306.43 | 284.1873 | 101.7406 |
| | 336.236 | 134.8632 | 238.2528 | 62.0022 | 52.4386 | 265.3086 | 207.9937 |
| | 209.301 | 178.7826 | 233.8236 | 87.1864 | 64.4478 | 314.4015 | 358.8314 |
| | 58.9266 | 147.938 | 190.624 | 152.2871 | 210.4621 | 178.1868 | 166.7008 |
| | 138.679 | 268.91 | 293.5415 | 86.1642 | 244.3336 | 317.9615 | 309.0982 |
| | 102.244 | 284.8372 | 275.6984 | 116.2768 | 16.8304 | 44.6235 | 287.5805 |
| | 113.8616 | 110.382 | 340.1102 | 351.1491 | 10.7875 | 158.4183 | 209.7066 |
| | 142.6375 | 121.5415 | 98.5186 | 252.8721 | 194.7434 | 90.792 | 203.6752 |
| | 71.887 | 359.0988 | 63.3173 | 204.2661 | 174.1397 | 140.1879 | 114.4883 |
| | 116.6258 | 32.3102 | 103.9045 | 243.8619 | 260.3113 | 190.5566 | |

FIG. 17

TABLE 8 - EXCITATION PULSE G

| NOS. | 1-19 | 20-38 | 39-57 | 58-76 | 77-95 | 96-110 |
|---|---|---|---|---|---|---|
| PHASE (°) | 81.7668 | 4.5141 | 291.1988 | 42.3627 | 168.8325 | 210.6353 |
| | 225.5463 | 93.6234 | 235.3771 | 117.7814 | 60.1639 | 199.3544 |
| | 282.0377 | 261.2157 | 236.5507 | 163.8286 | 174.7943 | 243.182 |
| | 244.1176 | 315.7233 | 97.8867 | 284.9423 | 201.1079 | 173.8407 |
| | 357.5861 | 65.237 | 37.6022 | 334.5463 | 127.4179 | 133.2879 |
| | 9.2846 | 1.6607 | 61.2449 | 270.6472 | 121.9252 | 119.4917 |
| | 96.5238 | 26.5461 | 105.0678 | 309.6836 | 90.8641 | 18.3762 |
| | 124.8582 | 126.5098 | 358.0544 | 293.0444 | 267.8137 | 64.3826 |
| | 161.7508 | 276.8261 | 348.9121 | 270.3089 | 14.7643 | 357.9163 |
| | 120.1958 | 148.3731 | 341.8969 | 277.4102 | 245.514 | 345.9993 |
| | 179.7277 | 257.8936 | 346.4019 | 62.216 | 162.9207 | 344.3665 |
| | 251.3558 | 252.6071 | 40.7659 | 7.3342 | 3.3849 | 267.517 |
| | 356.5659 | 9.1327 | 31.2454 | 8.2965 | 204.2489 | 288.9852 |
| | 294.8108 | 1.539 | 247.935 | 163.4907 | 199.6887 | 257.0847 |
| | 320.9232 | 199.8722 | 337.0521 | 202.0263 | 323.7548 | 150.4294 |
| | 9.793 | 293.6796 | 344.1938 | 295.6355 | 254.7513 | |
| | 79.7551 | 165.6382 | 191.7059 | 203.3388 | 144.4265 | |
| | 295.7179 | 358.4403 | 107.5109 | 119.8432 | 299.1465 | |
| | 260.8251 | 256.4382 | 73.3511 | 114.2859 | 273.3862 | |

*FIG. 18*

TABLE 9 – SNR

| SEQUENCE | SEGMENT LENGTH ($XT_{180}$) | NUMBER OF SEGMENTS | TOTAL PULSE LENGTH ($XT_{180}$) | SIMULATED SNR (POWER UNITS) | MEASURED SNR (POWER UNITS) |
|---|---|---|---|---|---|
| RECT (90) / RECT (180) | 0.5 | 1 | 0.5 | 1 | 1 |
| RECT (90) / RECT (135) | 0.5 | 1 | 0.5 | 1.13 | 1.14 |
| EXCITATION A / RPP-1.0 | 0.1 | 100 | 10 | 2.74 | 2.77 |
| EXCITATION B / RPP-1.0 | 0.078 | 162 | 12.64 | 3.21 | 3.13 |
| EXCITATION B / RPP-1.0 | 0.078 | 202 | 15.76 | 3.19 | 3.11 |
| EXCITATION D / RPP-1.0 | 0.078 | 156 | 12.17 | 3.11 | 3.07 |
| EXCITATION E / RPP-1.0 | 0.078 | 144 | 11.23 | 3.06 | 3.09 |
| EXCITATION F / RPP-1.0 | 0.078 | 132 | 10.3 | 2.92 | 2.95 |
| EXCITATION G / RPP-1.0 | 0.078 | 110 | 8.58 | 2.85 | 2.9 |
| THRESHOLD / RPP-1.0 | | | | 3.31 | |

FIG. 19

| TABLE 10 | | | | |
|---|---|---|---|---|
| SEGMENT NUMBER | CP-M8 | CP-M10 | CP-M12 | CP-M15 |
| 1 | 0.2945 | 1.2044 | 0.1982 | 0.2259 |
| 2 | 0.5915 | 0.6404 | 0.8469 | 0.6202 |
| 3 | 0.5814 | 0.5480 | 0.5325 | 0.3048 |
| 4 | 0.2722 | 1.1223 | 0.7463 | 0.1140 |
| 5 | 0.2980 | 0.5868 | 2.5463 | 0.3509 |
| 6 | 0.6183 | 0.1334 | 0.8385 | 0.6763 |
| 7 | 0.6831 | 0.1350 | 0.1057 | 0.9944 |
| 8 | 0.4971 | 1.7244 | 1.6332 | 0.4963 |
| 9 | 0.4719 | 0.4776 | 0.6621 | 0.6144 |
| 10 | 0.5886 | 0.2870 | 0.9377 | 0.2257 |
| 11 | 0.9274 | 0.8777 | | 0.1464 |
| 12 | 0.7209 | 0.1003 | | 1.2795 |
| 13 | 1.1535 | 0.5462 | | 0.3457 |
| 14 | 0.4192 | 0.5475 | | 0.5091 |
| 15 | 1.7249 | 0.2827 | | 1.6656 |
| 16 | 0.1345 | 0.2332 | | 0.5545 |
| 17 | 0.6141 | 1.1304 | | 0.4395 |
| 18 | 0.1013 | 0.7531 | | 1.2264 |
| 19 | 0.8818 | 0.9510 | | 0.6722 |
| 20 | 0.7655 | 0.1562 | | 0.9251 |
| TOTAL | 12.337 | 12.438 | 9.047 | 12.387 |

*FIG. 21*

| TABLE 11 | | | |
|---|---|---|---|
| PULSE NAME | PEAK AMPLITUDE | SQUARED INTEGRAL | HALF-POWER BANDWIDTH (UNITS OF $\omega_1$) |
| RECTANGULAR | 1 | 1 | 0.94 |
| CP-M8 | 2.0705 | 1.6589 | 3.34 |
| CP-M10 | 1.5244 | 1.4901 | 3.48 |
| CP-M12 | 1.6870 | 1.2902 | 2.60 |
| CP-M15 | 20.585 | 1.6369 | 3.16 |

REFOCUSING PULSES AND EXCITATION PULSES FOR NMR LOGGING

TECHNICAL FIELD

This invention relates to nuclear magnetic resonance (NMR) and, more particularly, to using nuclear magnetic resonance (NMR) for determining characteristics of substances.

BACKGROUND

General background of nuclear magnetic resonance (NMR) well logging is set forth, for example, in U.S. Pat. No. 5,023,551. Briefly, in conventional NMR operation, the spins of nuclei align themselves along an externally applied static magnetic field. This equilibrium situation can be disturbed by a pulse of an oscillating magnetic field (e.g. a radio frequency (RF) pulse), which tips the spins away from the static field direction. After tipping, two things occur simultaneously. First, the spins precess around the static field at the Larmor frequency, given by $\omega_0 = \gamma \times B_0$, where $B_0$ is the strength of the static field and $\gamma$ is the gyromagnetic ratio. Second, the spins return to the equilibrium direction according to a decay time $T_1$, which is called the longitudinal relaxation time constant or spin lattice relaxation time constant. For hydrogen nuclei, $\gamma/2\pi = 4258$ Hz/Gauss, so, for example, for a static field of 235 Gauss, the frequency of precession would be 1 MHz. Also associated with the spin of molecular nuclei is a second relaxation time constant, $T_2$, called the transverse relaxation time constant or spin-spin relaxation time constant. At the end of a ninety degree tipping pulse, all the spins are pointed in a common direction perpendicular to the static field, and they all precess at the Larmor frequency. The net precessing magnetization decays with a time constant $T_2$ because the individual spins rotate at different rates and lose their common phase. At the molecular level, dephasing is caused by random motions of the spins. The magnetic fields of neighboring spins and nearby paramagnetic centers appear as randomly fluctuating magnetic fields to the spins in random motion. In an inhomogeneous field, spins at different locations precess at different rates. Therefore, in addition to the molecular spin-spin relaxation of fluids, spatial inhomogeneities of the applied field also cause dephasing. Spatial inhomogeneities in the field can be due to microscopic inhomogeneities in the magnetic susceptibility of rock grains or due to the macroscopic features of the magnet.

A widely used technique for acquiring NMR data, both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one-hundred-eighty degree pulse is applied to cause the spins which are dephasing in the transverse plane to refocus. By repeatedly refocusing the spins using one-hundred-eighty-degree pulses, a series of "spin echoes" appear, and the train of echoes is measured and processed. The transverse relaxation time constant, $T_2$, or the distribution of multiple $T_2$s, can be obtained using this technique. In well logging, the CPMG sequence is traditionally executed using a set of equipment located "down-hole" in a well bore (in situ). While performing the CPMG sequence in situ allows for relatively rapid data gathering, limitations of the equipment and the environment can make it difficult to obtain accurate down-hole data. For example, due to the limits on equipment power, design constraints and down-hole conditions, the signal to noise ratio (SNR) for an in situ CPMG sequence remains low. This low SNR can impede the gathering and analysis of useful data about the formation in the ground.

SUMMARY

Illustrative embodiments are directed to applying a nuclear magnetic resonance (NMR) sequence to a substance within an inhomogeneous static magnetic field. Various embodiments can include applying a series of refocusing pulses to the substance, each refocusing pulse in the series of refocusing pulses having at least two segments, and a total pulse duration less than or equal to approximately 1.414 times $T_{180}$. As used herein:

$$T_{180} = \pi/(\gamma \times B_1);$$

where $\gamma$ is the gyromagnetic ratio of a particle in the substance within the inhomogeneous static magnetic field, and $B_1$ is the maximum amplitude of the applied radio frequency (RF) field in the area of interest within the substance.

Various embodiments can further include applying an excitation pulse to the substance in the inhomogeneous static magnetic field, where the excitation pulse generates an initial magnetization that is aligned with a refocusing axis produced by a refocusing cycle that is performed after the excitation pulse. The refocusing cycle includes a series of the refocusing pulses disclosed herein.

Illustrative embodiments are directed to a method for applying an NMR sequence. The method includes applying a series of refocusing pulses to a substance within an inhomogeneous static magnetic field, each refocusing pulse in the series of refocusing pulses having at least two segments, and a total pulse duration less than or equal to approximately 1.414 times $T_{180}$.

Various embodiments are directed to a method for applying an (NMR) sequence. The method includes applying a series of refocusing pulses to a substance within an inhomogeneous static magnetic field. Each refocusing pulse in the series of refocusing pulses can have the following properties: an initial segment and a final segment each having substantially equal durations, and a middle segment having a duration distinct from the initial and final segments. The initial segment, the middle segment, and the final segment each have a substantially constant amplitude, and a phase of the middle segment is shifted 180 degrees with respect to a phase of each of the initial segment and the final segment.

Illustrative embodiments are directed to a method for applying an NMR sequence. The method includes applying an excitation pulse to a substance within an inhomogeneous static magnetic field to induce a spin effect within the substance. The excitation pulse includes a plurality of segments. The method can further include applying a refocusing cycle to the substance, where the refocusing cycle generates a magnetization in the substance that is aligned with a refocusing axis. The excitation pulse generates an initial magnetization that is aligned with the refocusing axis.

Various embodiments are directed to a method for applying an NMR sequence. The method includes applying an excitation pulse to a substance within an inhomogeneous static magnetic field to induce a spin effect within the substance. The excitation pulse includes a plurality of segments, where each of the segments has a substantially constant amplitude. Further, each of the segments has one phase selected from no more than two distinct phases. The method further includes applying a series of refocusing pulses to the substance within the inhomogeneous static magnetic field after application of the excitation pulse.

BRIEF DESCRIPTION OF THE DRAWINGS

Further features and advantages will become more readily apparent from the following detailed description when taken in conjunction with the accompanying drawings.

FIG. 3 shows a plot of a conventional refocusing pulse and a plurality of refocusing pulses in accordance with various embodiments of the disclosure;

FIG. 12 shows Table 2, which include phase values (in degrees) for each segment of excitation pulse A, in accordance with various embodiments of the present disclosure;

FIGS. 13-18 shows Tables 3-8, which include phase values (in degrees) for each segment of excitation pulse B, C, D, E, F, and G, respectively, in accordance with various embodiments of the present disclosure;

FIG. 19 shows Table 9, which compares simulated and measured SNR for various embodiments of the present disclosure;

FIG. 21 shows Table 10, which includes segment lengths of excitation pulses in accordance with various embodiments of the disclosure;

It is understood that the drawings of the disclosure are not necessarily to scale.

DETAILED DESCRIPTION OF THE INVENTION

As noted herein, using CPMG sequences to obtain data about substances can be limited by a low signal-to-noise ratio (SNR). In contrast to conventional approaches, some embodiments of the invention include utilizing excitation and/or refocusing pulses to improve the SNR in CPMG sequencing, while maintaining the conventional output power of the pulsing equipment. In various embodiments, a class of refocusing pulses disclosed herein nearly doubles the SNR in a CPMG sequence as compared to the conventional approach. Additionally, in some embodiments, an excitation pulse is utilized which can optimize the SNR gain of the refocusing pulse and can augment the size of the reliable sample slice in the substance.

Figure 1:
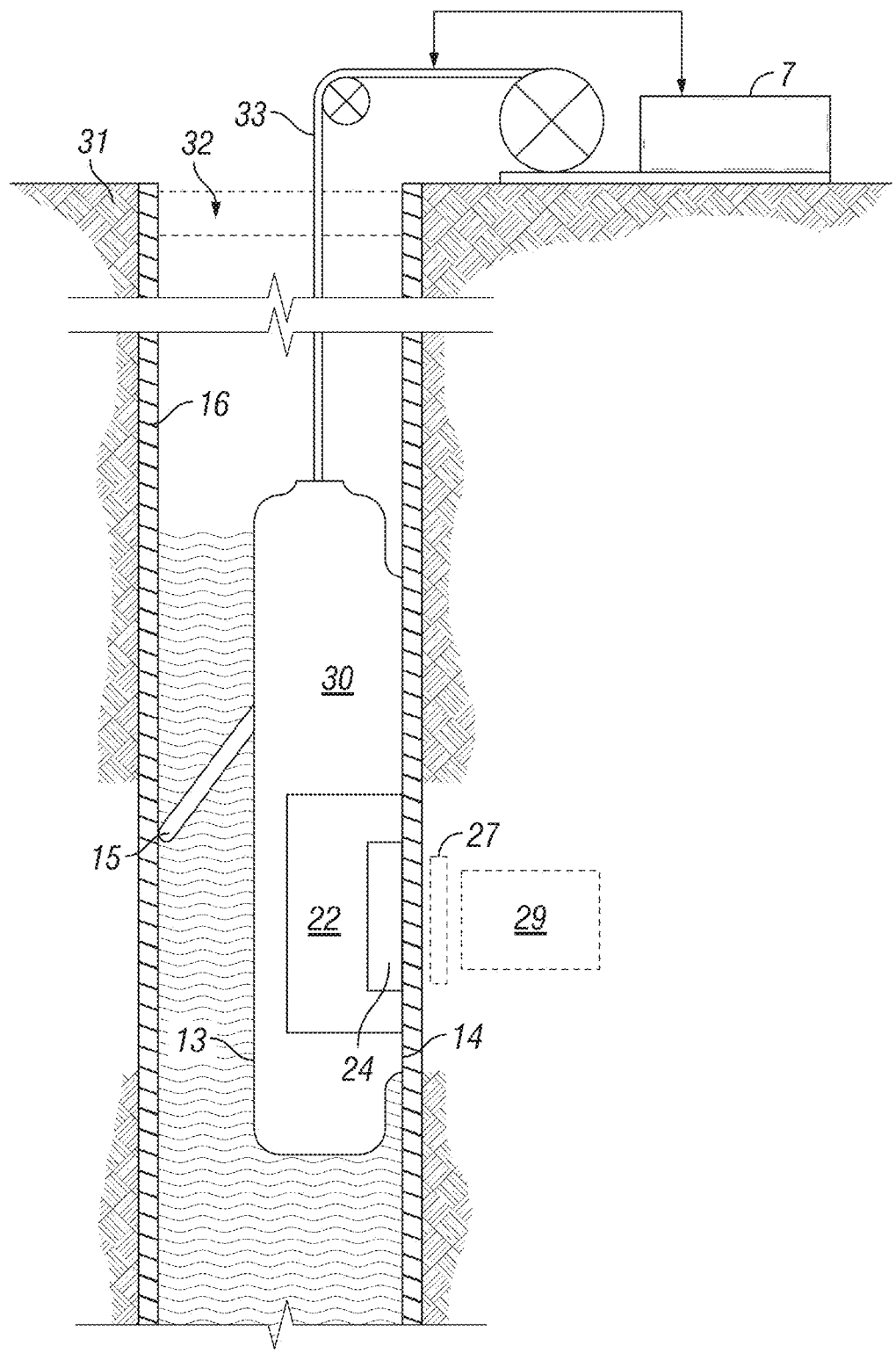
FIG. 1 shows a schematic diagram, partially in block form, of a well logging apparatus that can be used in practicing some embodiments of the disclosure.

Various embodiments of the invention can be employed using a well logging apparatus to investigate, in situ, a region of earth formations surrounding a borehole to determine a characteristic of the region (including e.g., rock, liquid, or some other substance or material). FIG. 1 illustrates an embodiment of such an apparatus for investigating subsurface formations 31 traversed by a borehole 32. A magnetic resonance investigating apparatus or logging device 30 is suspended in the borehole 32 on an armored cable 33, the length of which substantially determines the relative depth of the device 30. The length of cable 33 is controlled by suitable means at the surface such as a drum and winch mechanism (not shown). Surface equipment, represented at 7, can be of conventional type, and can include a processor subsystem in communication with the downhole equipment. The processor subsystem may be any suitable NMR equipment of conventional type that can produce a substantially uniform static magnetic field and can produce radio frequency (RF) pulses at controlled times and of controlled frequency, phase, and duration as described herein. It will be understood that processing can be performed downhole and/or uphole, and that some of the processing may be performed at a remote location. Also, while a wireline is illustrated, alternative forms of physical support and communicating link can be used, for example in a measurement while drilling system (e.g., logging-while-drilling). As described for example in the U.S. Pat. No. 5,055,787, the magnetic resonance logging device 30 can have a face 14 shaped to intimately contact the borehole wall, with minimal gaps or standoff. The borehole wall may have a mudcake 16 thereon. A retractable arm 15 can be provided which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging tools.

The logging device includes, for example, a permanent magnet or permanent magnet array 22, which may comprise samarium-cobalt magnetic material, and one or more RF antennas 24, which may be a suitably oriented coil or coils. A sensitivity zone, represented generally at 27, is a region in the subsurface formations 31 in which the static magnetic field is substantially uniform. An area of interest, represented generally at 29, is a region in the subsurface formations 31 in which the static magnetic field is inhomogeneous.

Figure 2:
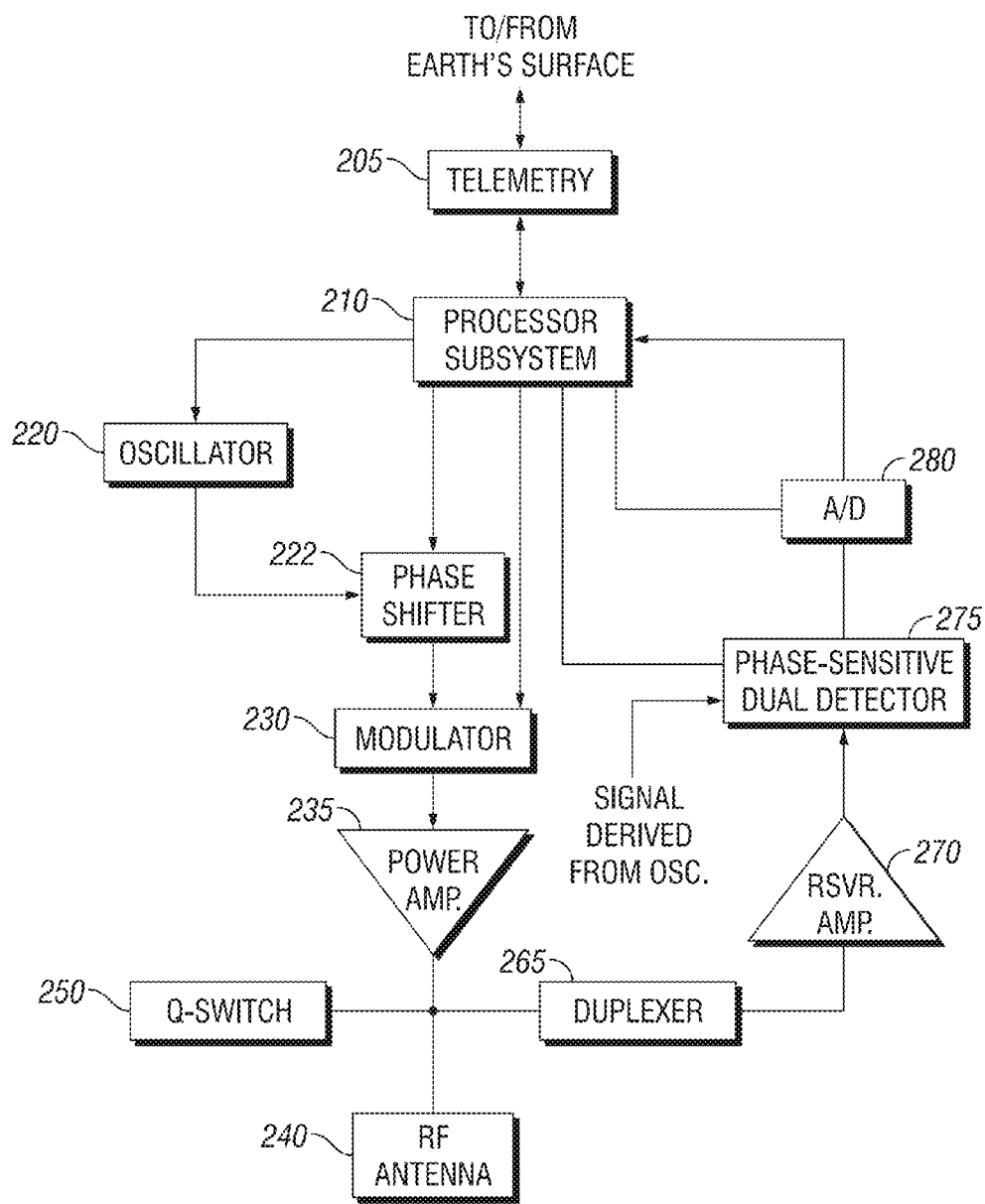
FIG. 2 shows a block diagram of downhole circuitry in accordance with various embodiments of the disclosure.

FIG. 2 shows, in simplified form, circuitry of a type that can be used for producing RF pulse sequences and for receiving and processing NMR signals as described herein. In FIG. 2, a downhole processor subsystem is represented at 210. The processor subsystem 210 has associated memory, timing, interfaces, and peripherals (not separately shown), as is well known in the art. The processor subsystem 210 is conventionally coupled with telemetry circuitry 205, for communication with the earth's surface. An oscillator 220 produces radio frequency (RF) signals at the desired resonant frequency or frequencies in the investigation region, and the output of the oscillator is coupled to a phase shifter 222 and then to a modulator 230, both of which are under control of the processor subsystem 210. The phase shifter 221 and modulator 230 can be controlled, in a manner known in the art, to produce the desired pulses of RF field, for example the excitation and refocusing pulses utilized in embodiments of the present invention. As described, for example, in U.S. Pat. No. 5,055,788, the oscillator 220 can include a plurality of oscillators used in a manner that facilitates the generation and ultimate detection of the desired signals. The output of modulator 230 is coupled, via a power amplifier 235, to an RF antenna 240. A Q-switch 250 can be provided to critically damp the RF antenna system to reduce antenna ringing. The antenna 240 is also coupled with a receiver section via a duplexer 265, the output of which is coupled to a receiver/amplifier 270. The duplexer 265 protects the receiver/amplifier 270 from high power pulses which pass to the RF antenna 240 during the transmitting and damping modes.

During the receiving mode, the duplexer 265 is effectively just a low impedance connection from the antenna 240 to the receiver amplifier 270. The output of the receiver amplifier 270 is coupled to a dual phase-sensitive detector 275, which also receives, as a reference, a signal derived from the oscillator signal. The detected output is coupled to an analog-to-digital converter 280, the output of which is a digital version of the received nuclear magnetic resonance signal.

While some embodiments of the invention are described with respect to down-hole or wireline NMR processes, where the substance of interest is located outside the RF antenna (e.g., outside the coil), other embodiments of the invention can be applied to a downhole fluid analysis (DFA) technique, including the use of a flow-line analyzer. In such embodiments, the substance of interest may be located and analyzed inside a coil. In some embodiments, the coil generates a static field that is applied to the substance of interest. Various embodiments of the invention can yield benefits in such deployments as well as in the down-hole or wireline NMR processes. Additionally, many of the embodiments disclosed herein can be applied to surface-based NMR techniques. Even further, aspects of the invention can be applied to any NMR process performed in an inhomogeneous static magnetic field. That is, various embodiments can be applied to NMR processes performed proximate to a substance of interest, where that substance is located in an inhomogeneous magnetic field. Specific examples of NMR processes should not be considered limiting of the invention described herein.

Refocusing Pulses

Various embodiments of the invention include applying novel types of composite refocusing pulses in an inhomogeneous field, which is a typical condition for NMR well logging. In some embodiments, the refocusing pulses have three segments that take the form of: $\alpha_{\phi+\pi}-\beta_\phi-\alpha_{\phi+\pi}$, where $\beta$ and $\beta$ are nutation angles for each segment and $\phi$ is the relative phase of each segment. In some embodiments, two of the segments (e.g., $\alpha$ and $\alpha$) are of substantially equal pulse length. Also, in some embodiments, the middle segment (e.g., $\beta$) is phase shifted approximately 180-degrees from each of the preceding segment and the following segment (e.g., the middle segment is reverse-phase). According to various embodiments, the phases are not required to correspond precisely with the stated values (e.g., 0-degrees or 180-degrees). Small modifications to the phase can be made that will still achieve some of the advantages of the invention. Furthermore, various embodiments of the present invention are not limited to phase shifting by 180-degrees. In some embodiments of the present invention, the segments of the refocusing pulse are phase shifted by a different value (e.g., 90-degrees, 150-degrees, 160-degrees or 170-degrees). Any such "rotated-phase" refocusing pulses (e.g., 150-degrees or 180-degrees) are referred to herein as RPP pulses. Such RPP pulses can replace the conventional $\pi_\phi$ refocusing pulse in the conventional CPMG sequence ($\pi$ is known and referred to herein as 180-degrees).

Three example RPP pulses in accordance with some embodiments of the present invention are disclosed, and are referred to as:

$$\text{RPP-1.0}\{\alpha,\beta\}\approx\{0.14\pi, 0.72\pi\}$$

$$\text{RPP-1.3}\{\alpha,\beta\}\approx\{0.2\pi, 0.9\pi\}$$

$$\text{RPP-1.9}\{\alpha,\beta\}\approx\{0.3\pi, 1.3\pi\}$$

It is understood that these pulses are merely example pulses, and that a number of combinations of $\alpha$ and $\beta$ values can be used in accordance with various aspects of the invention. In contrast to the exemplary pulses, a conventional refocusing pulse corresponds to, $\alpha=0$, $\beta=\pi$ and has a total length of $T_{180}$ (e.g., a rectangular pulse). As used herein, the pulse duration $T_{180}$ is defined as: $T_{180}=\pi/(\gamma\times B_1)$; where $\gamma$ is the gyromagnetic ratio of a particle in the substance within the inhomogeneous static magnetic field, and $B_1$ is the maximum amplitude of the applied radio frequency (RF) field in the area of interest within the substance. Furthermore, as used herein $T_{90}$ is defined as: $T_{90}=\pi/2(\gamma\times B_1)$.

FIG. 3 shows graphical representations of respective profiles of a prior art rectangular refocusing pulse (a), and three illustrative RPP refocusing pulses according to embodiments of the invention (b), (c) and (d) are shown. As shown, the refocusing pulses can utilize the same RF amplitude (y-axis, "A") as in the prior art refocusing pulse. Illustrative embodiments of the present invention include RPP refocusing pulses with different pulse lengths. For example, the RPP pulses can be of a substantially similar pulse length (x-axis) as the prior art pulse (e.g., RPP-1.0), minimally longer than the prior art pulse (e.g., RPP-1.3), or minimally shorter than the prior art pulse. In this manner, the RPP pulses require similar power usage and ability to measure short relaxation times, as compared to the conventional pulse.

In further illustrative embodiments, a series of refocusing pulses (e.g., RPP pulses) in an NMR sequence is performed in an inhomogeneous static magnetic field. Each refocusing pulse in the series of RPP pulses has at least two segments, indicated by S and a corresponding number in FIG. 3. In the examples of FIG. 3, each RPP pulse is shown including three segments, S1, S2 and S3. As noted herein, in some embodiments, each RPP pulse in the series of RPP pulses can have a total pulse duration (a sum of all the segments) less than or equal to approximately 1.414 (the square root of 2) times $T_{180}$. For instance, in the case of RPP-1.0 and RPP-1.3 pulses, the total pulse duration of all three segments S1, S2 and S3 is approximately 1.0 times $T_{180}$ and approximately 1.3 times $T_{180}$, respectively. In the case of the RPP-1.9 pulse, the total duration is $1.9 \times T_{180}$. In various embodiments, the total pulse duration is less than or equal to $1.0 \times T_{180}$, $1.414 \times T_{180}$, $2.0 \times T_{180}$, $4.0 \times T_{180}$, or $8.0 \times T_{180}$. In other embodiments, the total pulse duration ranges between $0.1 \times T_{180}$ and $1.0 \times T_{180}$.

In some embodiments, each of the at least two segments (e.g., S1, S2, S3) of the RPP pulse can have a phase of either zero degrees or 180 degrees. FIG. 3 illustrates that each middle segment S2 in the RPP pulses has a phase of approximately 180 degrees. Each initial (S1) and final (S3) segment, respectively, has a phase of approximately 0-degrees. Not all phase indicators (e.g., S1 and S3 in FIG. 3(b)) are labeled for clarity of illustration.

In another illustrative embodiment, the RPP pulse includes two segments. One of the two segments has a phase of 0-degrees and the other segment has a phase of 180-degrees (not shown). Such an embodiment has a total pulse length of less than approximately $1.414 \times T_{180}$. In yet another illustrative embodiment, the RPP pulse includes four segments. In such an embodiment, a first and third segment may have phases of 0-degrees and a second and a fourth segment may have phases of 180 degrees (not shown). Various embodiments of the invention may include more than four segments (e.g., 5, 10, 20 segments) with a number of different types of phase arrangements. In specific embodiments, the RPP pulses include four or more segments and the first three segments take the form of $\alpha_{\phi+\pi}-\beta_\phi-\alpha_{\phi+\pi}$, while the segments that follow the first three take a different form (e.g., constant phase).

In further illustrative embodiments, each of the at least two segments (e.g., S1, S2, S3) of the RPP refocusing pulse has a substantially constant amplitude (e.g., "A" or "−A"). In this case, the term "substantially constant" indicates that the amplitude of each segment of the RPP pulse remains within +/−10% of the overall pulse amplitude (A).

The methods according to certain embodiments of the invention can further include applying an excitation pulse to the substance within the inhomogeneous static magnetic field prior to applying the series of RPP pulses. Particular excitation pulses, which can be applied prior to the RPP pulses, are described in greater detail with reference to other embodiments below. It is understood that the overall NMR process according to various embodiments can include detecting NMR signals from the substance during application of the series of RPP pulses, such that applying the RPP pulses allows for data gathering about properties of the substance in the inhomogeneous field. In particular, detecting the NMR signals from the substance allows for determination of one or more characteristics of the substance.

Another method for applying an NMR sequence, in accordance with one embodiment, includes applying a series of refocusing pulses (e.g., RPP pulses) to a substance within an inhomogeneous static magnetic field. Referring again to FIG. 3, each of the RPP pulses (e.g., RPP-1.0, RPP-1.3, RPP-1.9, etc.) in the series of pulses includes an initial segment S1, a middle segment S2 and a final segment S3. In some embodiments, the initial segment S1 and the final segment S3 each have substantially equal durations ($T_\alpha$), and the middle segment S2 has a distinct duration ($T_\beta$) from the initial and final segments S1, S3. Furthermore, the initial segment S1, middle segment S2 and final segment S3 can have a substantially constant amplitude "A" as defined herein. Additionally, a phase of the middle segment S2 is shifted 180-degrees with respect to each of the initial segment S1 and the final segment S3.

In one case, a sum of the durations of the initial segment S1 ($T_\alpha$), the middle segment S2 ($T_\beta$) and the final segment S3 ($T_\alpha$) is less than or equal to approximately four times $T_{180}$.

In another case, a sum of the durations of the initial segment S1, the middle segment S2, and the final segment S3 is less than or equal to approximately two times $T_{180}$. Examples of this scenario are illustrated with respect to RPP-1.9, and RPP-1.3, in FIGS. 3(d) and 3(c), respectively.

Figure 4:
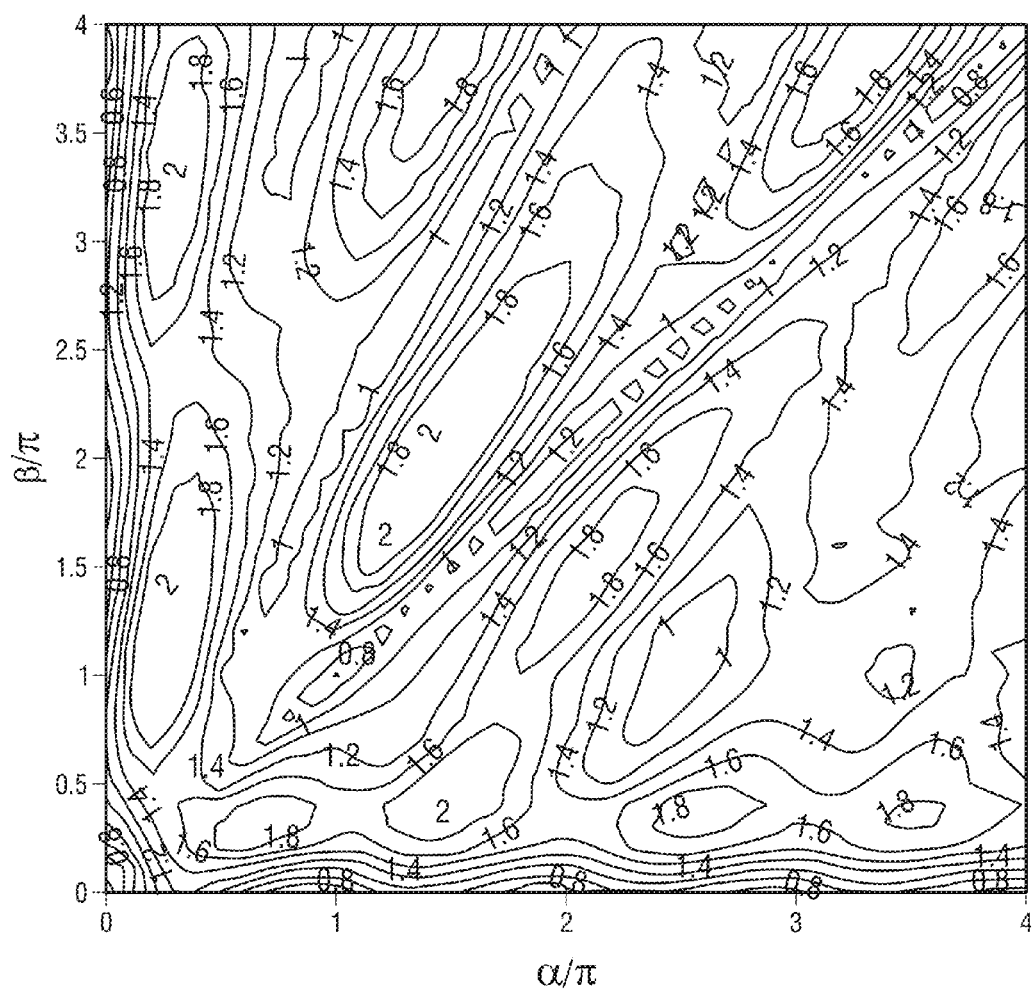
FIG. 4 shows a plot of segment values for refocusing pulses in accordance with various embodiments of the disclosure.
Figure 5A:
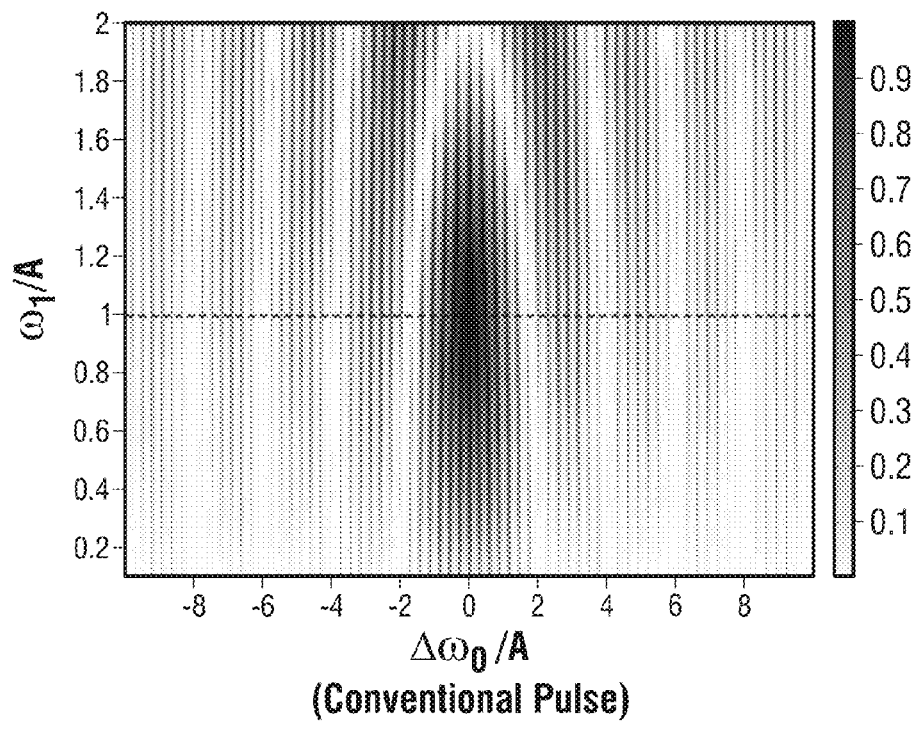
FIG. 5 shows a plot of pulse distributions for a conventional refocusing pulse and for a plurality of refocusing pulses in accordance with various embodiments of the disclosure.
Figure 5B:
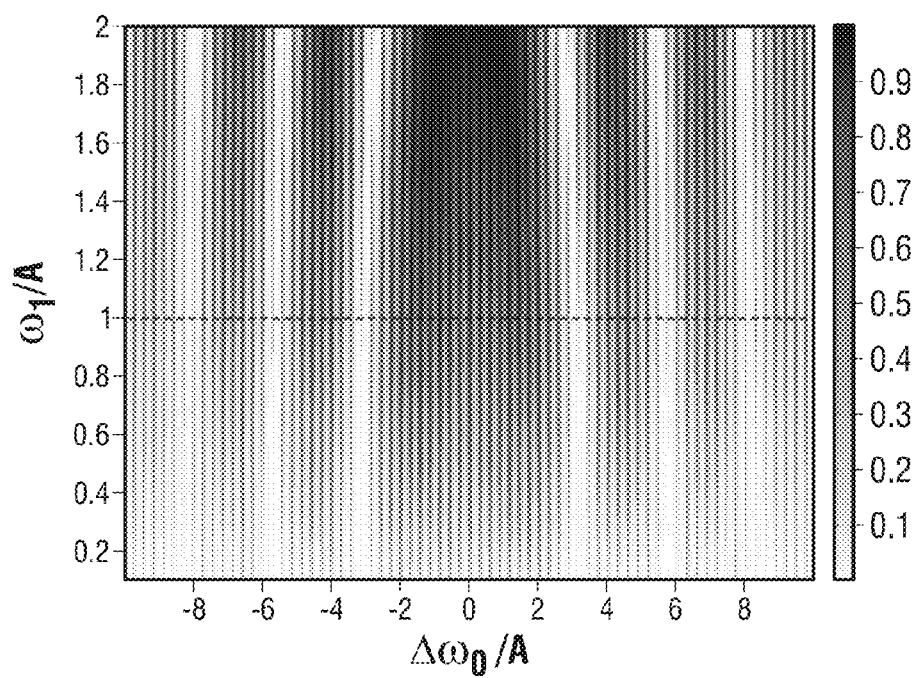
Figure 5C:
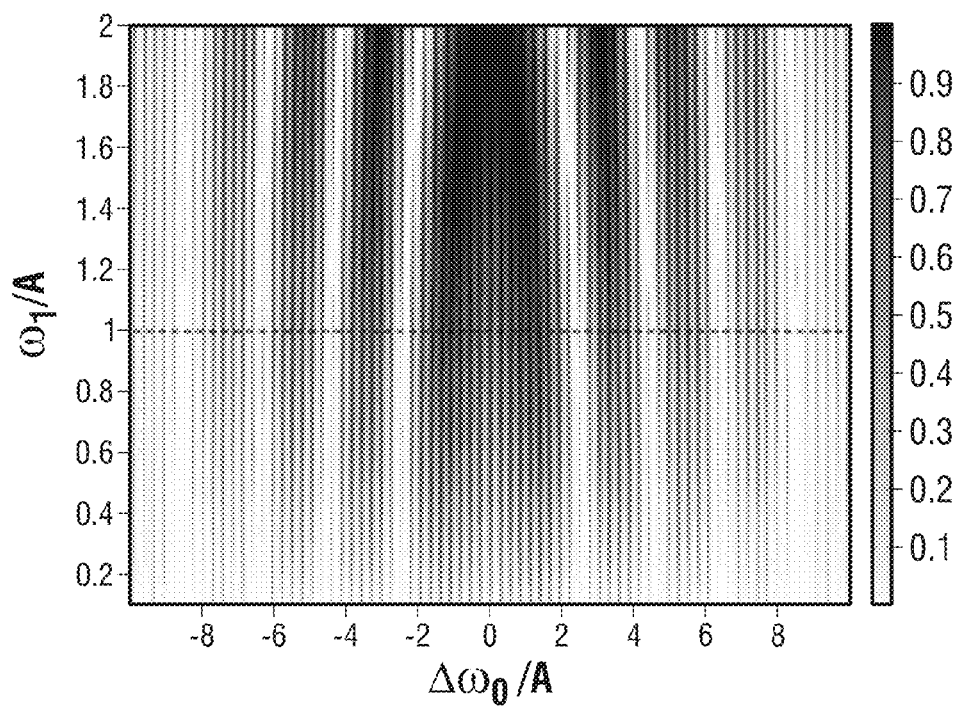
Figure 5D:
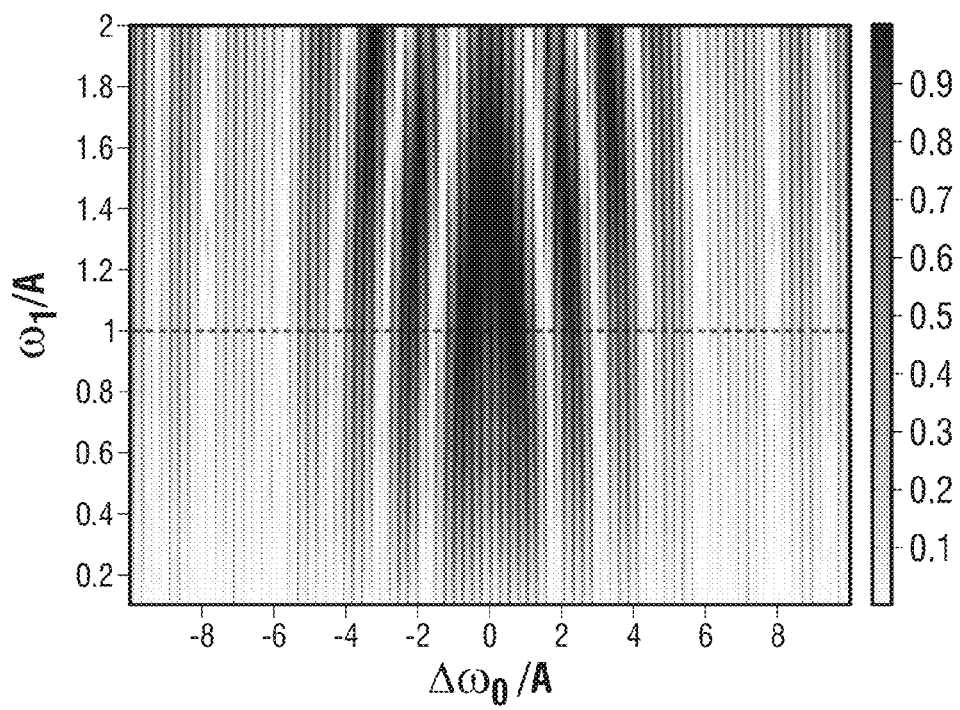
Figure 6A:
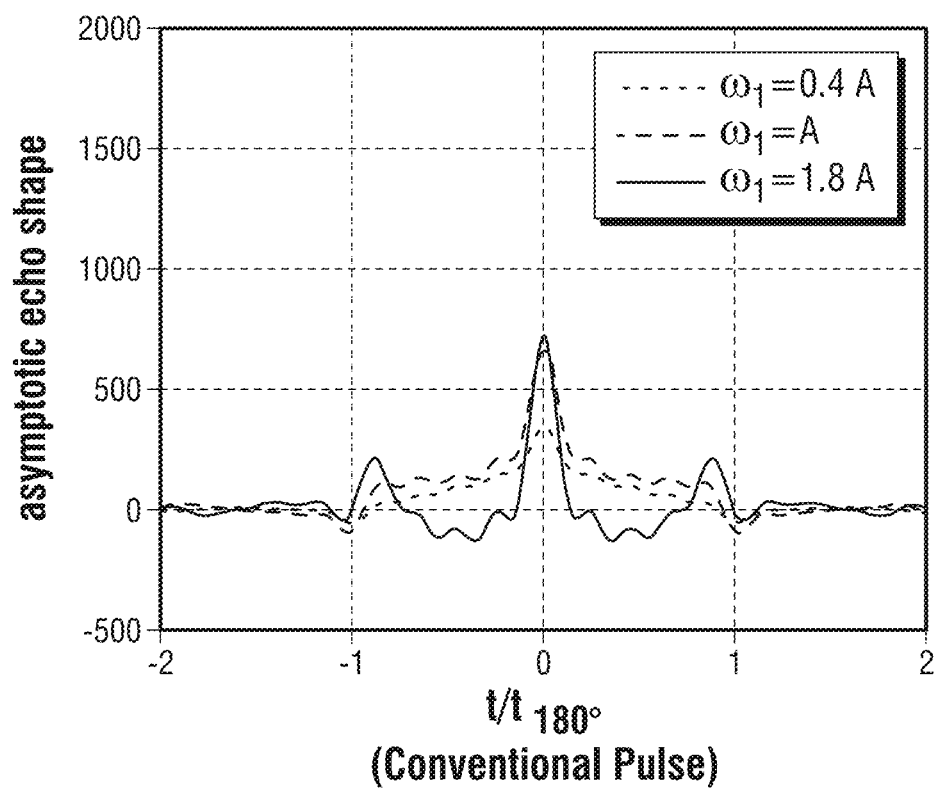
FIG. 6 shows a plot of echo shapes for a conventional refocusing pulse and for a plurality of refocusing pulses in accordance with various embodiments of the disclosure.
Figure 6B:
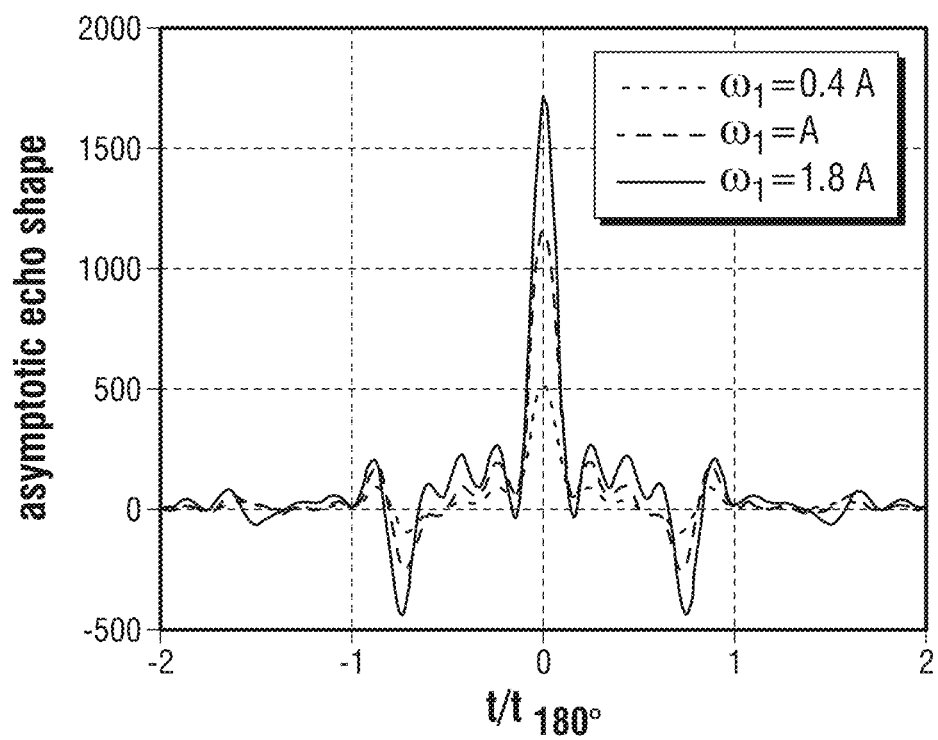
Figure 6C:
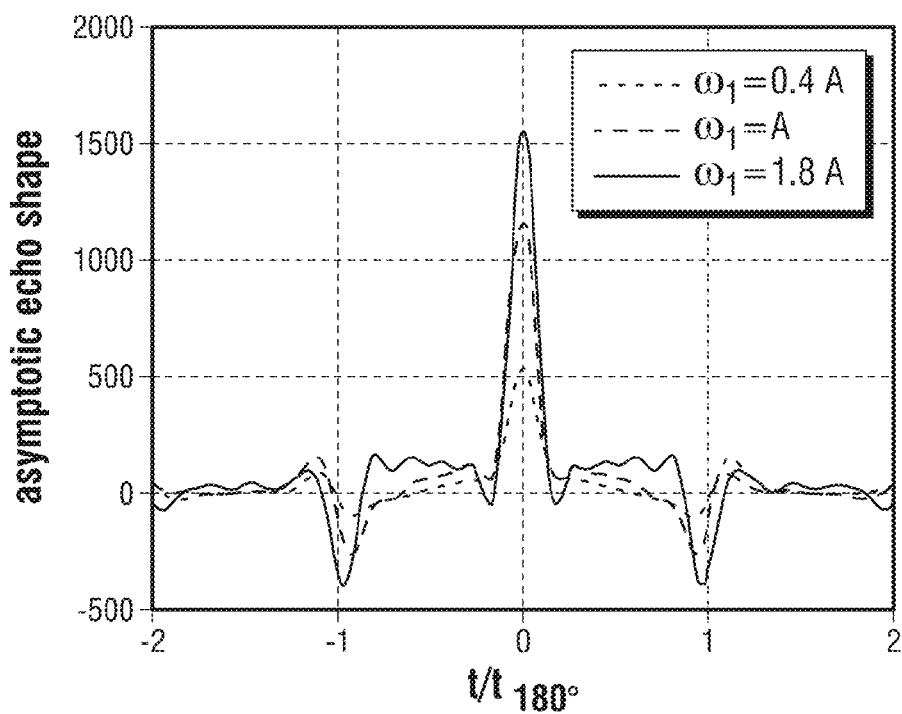
Figure 6D:
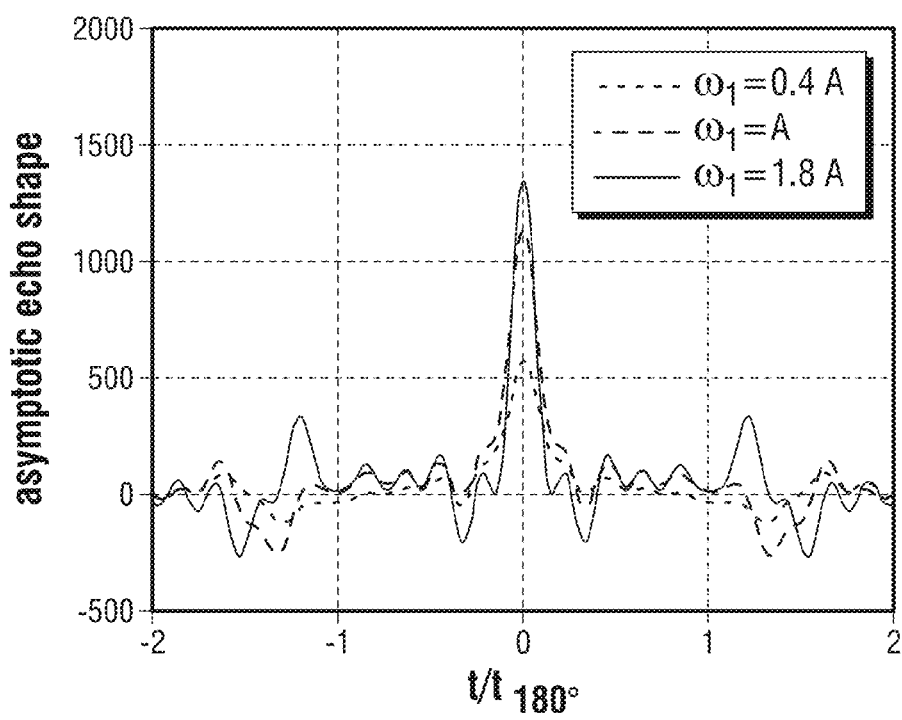

In yet another case, a sum of the durations of the initial segment S1 ($T_\alpha$), the middle segment S2 ($T_\beta$), and the final segment S3 ($T_\alpha$) is less than or equal to approximately $T_{180}$. One example of this scenario is illustrated with respect to RPP-1.0 in FIG. 3(b). In this particular embodiment (RPP-1.0), each RPP pulse in the series of pulses has an initial segment S1 and final segment S3 (designated as $\alpha$), each with a duration of approximately 0.14 times $T_{180}$, and a middle segment (designated as (3) with a duration of approximately 0.72 times $T_{180}$. In another example (RPP-1.3), each RPP pulse in the series of pulses has an initial segment S1 and final segment S3 (designated as $\alpha$), each with a duration of approximately 0.2 times $T_{180}$, and a middle segment (designated as (3) with a duration of approximately 0.9 times $T_{180}$. FIG. 4 shows a graphical representation of combinations of $\alpha$ and $\beta$ values in the RPP pulses in accordance with certain embodiments of the present invention. The areas with larger $\alpha$ and $\beta$ values (e.g., 2.0, 1.8. versus 1.2, 1.4) indicate improved performance relative to the conventional pulse.

As described herein, various embodiments of the invention are concerned with determining characteristics of a substance located within an inhomogeneous static magnetic field. The term "inhomogeneous" should be considered in the context of the NMR art. Many NMR well logging tools deploy inhomogeneous static magnetic fields due to the limitations and constraints of a borehole environment. In this context, an inhomogeneous static magnetic field is a static magnetic field that varies in intensity within an area of interest of a substance. In one example, an inhomogeneous static magnetic field may vary in intensity by a value approximately equal to or greater than a nominal amplitude of the series of RPP refocusing pulses, denoted as amplitude "A" in FIG. 3.

Illustrative embodiments of the present invention are also directed to determining characteristics of the refocusing pulses, such as an echo shape and an SNR for the refocusing pulses. The echo shape characteristics and the SNR can be used to optimize the refocusing pulses. Optimal control theory ("OCT") is one tool that can be used to determine pulse characteristics. In certain embodiments, characteristics for several different types of refocusing pulses can be determined and the refocusing pulses with the most desirable characteristics can be selected for use in an NMR tool. A method and process for determining refocusing pulse characteristics follows.

As noted herein, when the Larmor frequencies of spins are substantially inhomogeneous, as in, for example, NMR well logging, the spin echoes within the substance of interest go through transient states and quickly approach asymptotic form. One method for determining an asymptotic echo is to let $M(O^+)$ be the magnetization after the initial excitation pulse, and denote $\hat{n}=\hat{n}(\Delta\omega_0, \omega_1)$ as the axis of the effective rotation that describes the evolution from one echo to the next for a given value of $\omega_0$, (e.g., the offset in $B_0$, and $\omega_1$), the amplitude of the RF field $B_1$, and θ the angle of rotation. The magnetization at the $N^{th}$ echo can be decomposed into 3 components as:

$$\vec{M}_N = (\hat{n}\cdot\vec{M}(0^+))\hat{n} + \cos(N\theta)[\vec{M}(0^+) - (\hat{n}\cdot\vec{M}(0^+))\hat{n}] + \sin(N\theta)(\hat{n}\times\vec{M}(0^+)) \quad (1)$$

In sufficiently inhomogeneous fields and large enough echo numbers N, the second and third terms will average out and the asymptotic echo is given solely by the first term as:

$$\vec{M}_{asy}(\Delta\omega_0,\omega_1)=(\hat{n}\cdot\vec{M}(0^+))\hat{n} \quad (2)$$

To refocus spins initially along the x direction, a perfect excitation pulse (e.g., $M(O^+)=\hat{x}$ for all values of $\Delta\omega_0$ and $\omega_1$) can be used. In this case, the expression for the asymptotic magnetization simplifies to:

$$\vec{M}_{asy}(\Delta\omega_0,\omega_1)=n_x^2\hat{x} \quad (3)$$

An advantageous refocusing pulse can display $n_x^2=1$, over a very large region of the $(\Delta\omega_0, \omega_1)$ space. FIG. 5 shows a graphical representation of the distribution of $n_x^2$ for a plurality of RPP pulses in accordance with certain embodiments of the present invention. In this example, an echo spacing $T_E$ is chosen to be equal to $6\times T_{180}+T_P$, where $T_P$ is the corresponding refocusing pulse length. In various embodiments of the present invention, the echo spacing $T_E$ is the time period between a central portion of a first echo and a central portion of second echo. This time $T_E$ includes the pulse length $T_P$ and a free-precession period $T_{FP}$. Also, in this example, spacing between the application of two consecutive refocusing pulses, without including the refocusing pulse, is chosen to be equal to $6\times T_{180}$ and the "A" is the nominal RF amplitude.

FIG. 5 illustrates $n_x^2$ over field inhomogeneities for a conventional pulse and a plurality of RPP pulses. The sum of $n_x^2$ is the maximum possible normalized magnetization. As shown in the figure, compared to the conventional pulse, the in-phase magnetization (indicated by dark outlines) for the RPP pulses is greater in a larger region of field inhomogeneities. At the nominal RF frequency, the RPP pulses can focus more spins far off resonance. In various embodiments, the performance of the RPP pulses is slightly inferior in the close vicinity of resonance, but the RPP pulses compensate for this phenomenon with improved performance off-resonance.

Asymptotic echo shapes and SNR of the RPP pulses can be determined as follows. For a field inhomogeneity that is characterized by the distribution map $f(\omega_0, \Delta\omega_1)$, the asymptotic echo shape is given by:

$$M(t)=\iint d\Delta\omega_0 d\omega_1 e^{i\Delta\omega_0 t}(M_{asy,x}+iM_{asy,y})(\Delta\omega_0,\omega_1)f(\Delta\omega_0,\omega_1) \quad (4)$$

In this case, there is only the in-phase component, so equation (4) is simplified as:

$$M(t)=\iint d\Delta\omega_0 d\omega_1 e^{i\Delta\omega_0 t}n_x^2 f(\Delta\omega_0,\omega_1) \quad (5)$$

Using a matched filter and a constant noise spectrum density, the SNR is evaluated as:

$$SNR \propto \int_{T_{acq}/2}^{T_{acq}/2} M(t)^2 dt \quad (6)$$

where $T_{acq}$ is the acquisition time. In a constant $B_0$ gradient $f(\omega_0, \Delta\omega_1)\approx const \times f_1(\omega_1)$. In that case, the following equation applies:

$$M(t)=\int d\omega_1 f_1(\omega_1)\int d\omega_0 e^{i\omega_0 t}n_x^2(\omega_0,\omega_1)=\int d\omega_1 f_1(\omega_1)m(\omega_1,t). \quad (7)$$

FIG. 6 shows the echo shape $m(\omega_1, t)$ for different values of $\omega_1$. This figure illustrates the asymptotic echo shape for different pulses with RF inhomogeneity, assuming a perfect initial 90-degree pulse. In this case, 3126 spins were used in a constant gradient from [−10A, 10A], where "A" is the nominal RF amplitude. The echo peaks for the new RPP pulse are constantly high compared to that of the conventional pulse. In particular, the peak for RPP-1.0 increases as the RF amplitude increases.

Figures 7, 8:
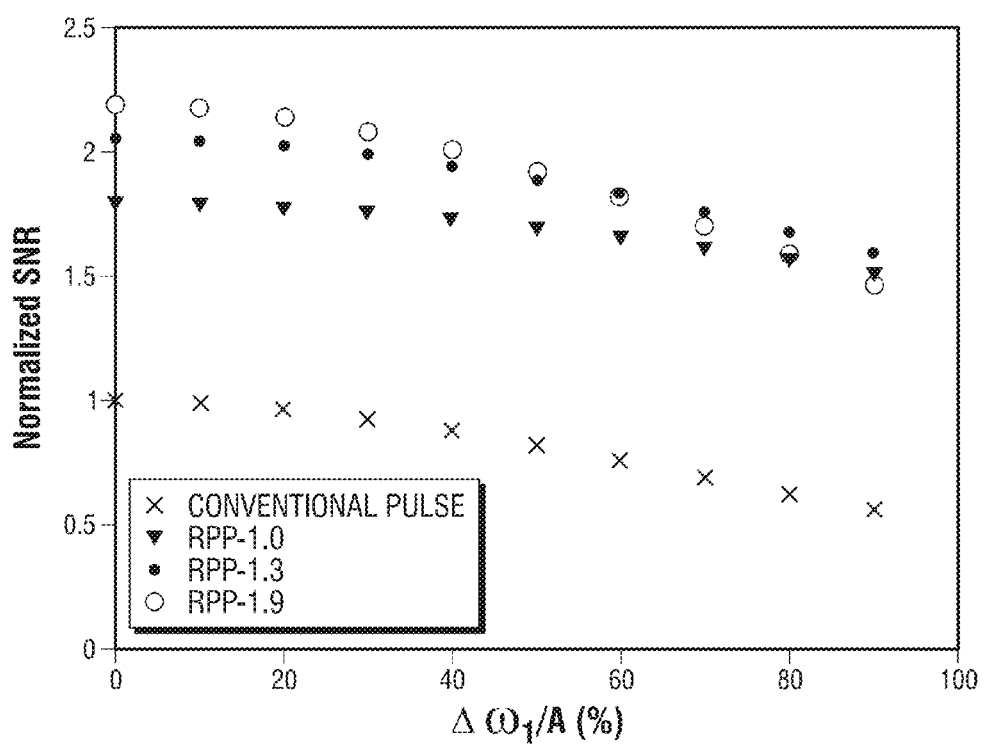
FIG. 7 shows Table 1, which shows signal-to-noise ratio (SNR), under two different assumptions of initial excitation, for a conventional refocusing pulse and for a plurality of refocusing pulses in accordance with various embodiments of the disclosure.
FIG. 8 shows a plot of SNR for a conventional refocusing pulse and for a plurality of refocusing pulses in accordance with various embodiments of the disclosure.

FIG. 7 shows Table 1, which illustrates the SNR for each of the conventional pulse, the RPP-1.0 pulse, the RPP-1.3 pulse, and the RPP-1.9 pulse, under two different initial excitations. The SNR is normalized with respect to an SNR for a rectangular 180-degree refocusing pulse with a perfect rectangular 90-degree excitation pulse.

FIG. 8 shows a graphical representation of SNR in the presence of RF inhomogeneity. The SNR for all four pulses is normalized with respect to an SNR for rectangular 180-degree refocusing pulses. In each case, a perfect rectangular 90-degree excitation pulse is used. "A" is the nominal RF amplitude. As shown, given a uniform distribution of RF inhomogeneity, the SNR stays consistently higher for the RPP pulses in the presence of RF inhomogeneity. In particular, RPP-1.0 is less sensitive to RF inhomogeneity than the conventional rectangular refocusing pulses. At 90% RF inhomogeneity, the rectangular pulse loses half of the nominal value, while the RPP pulses still produce an SNR 1.5 times the nominal value.

In some cases, an improved performance can be achieved by using excitation pulses that align initial magnetization with the effective refocusing axis n̂ of the refocusing pulses, as shown in Equation 2. Table 1 reports the improved potential performance of the RPP pulses at the nominal RF amplitude, when the initial magnetization is aligned with the refocusing axis. As shown, in some cases, the RPP refocusing pulses can yield a much higher SNR than the conventional rectangular refocusing pulse. This may be a result of, for example, the ability of the RPP pulses to refocus more spins outside the reach of the conventional rectangular pulse.

Figure 9:
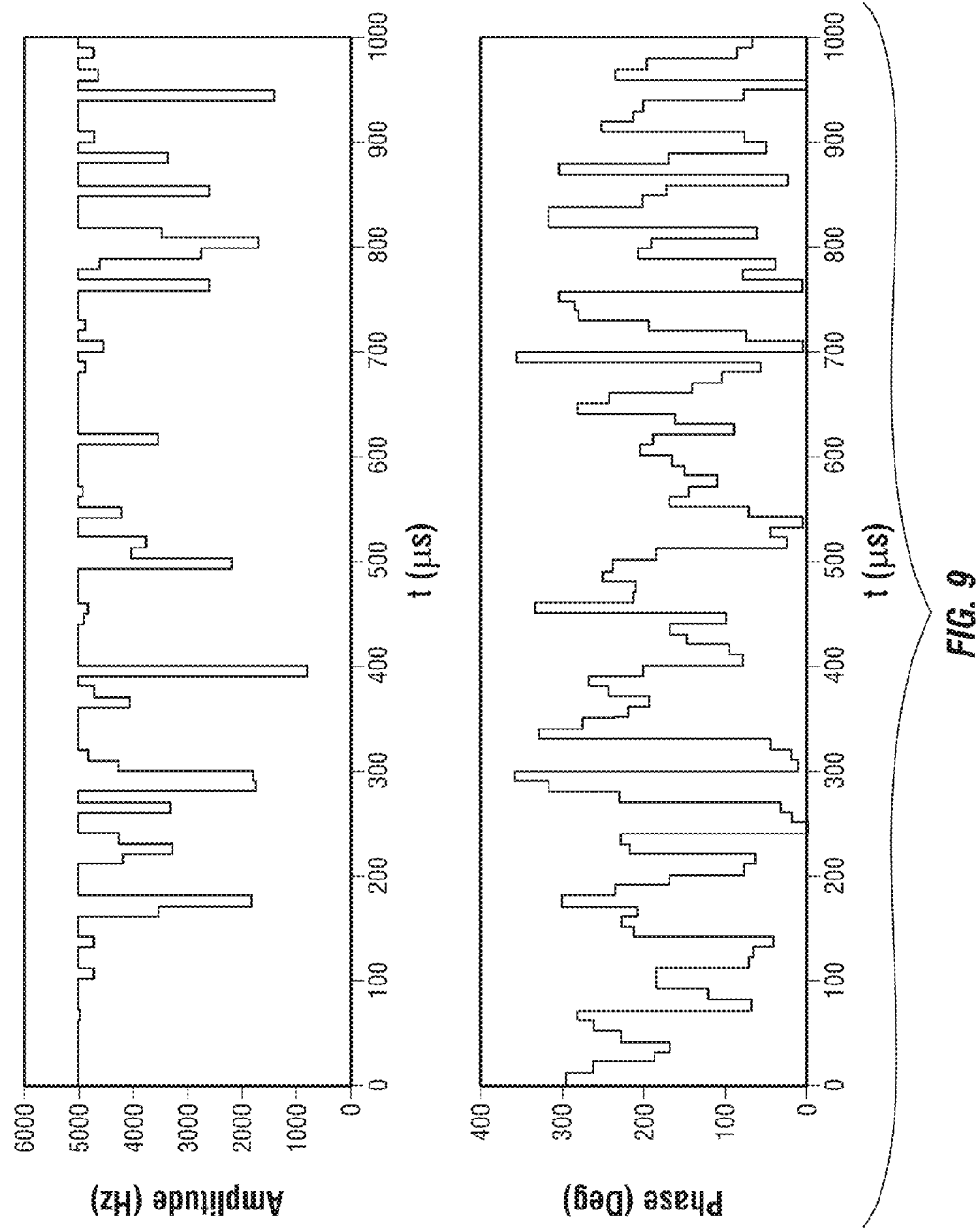
FIG. 9 shows a plot for an excitation pulse in accordance with various embodiments of the disclosure.

FIG. 9 provides an example of an initial excitation pulse for an RPP-1.0 refocusing pulse sequence. This example is provided using a nominal RF amplitude of A=5 kHz, $T_{180}$=200 us, and a pulse length of 1 ms. The excitation pulse is 20 times as long as a rectangular 90-degree pulse, but, because the excitation pulse is applied once for the acquisition of thousands of echoes, the difference in length is not a significant detriment. In combination with a series of RPP-1.0 refocusing pulses, this illustrative pulse produces an SNR that is 1.79 times the value of SNR for a series of rectangular refocusing pulses with a perfect 90-degree excitation.

In practice, the excitation pulse is neither a perfect 90-degree pulse nor is it able to align the spins precisely with their respective axes of rotation. With respect to conventional "non-perfect" excitation pulses currently used in well logging (e.g., a rectangular 90-degree pulse with a reduced free precession time before the first echo of $T_{180}/\pi$), the illustrative pulse produces an SNR that is 2.04 times the value of the convention pulse (e.g., a 100% improvement over conventional pulses).

Figure 10:
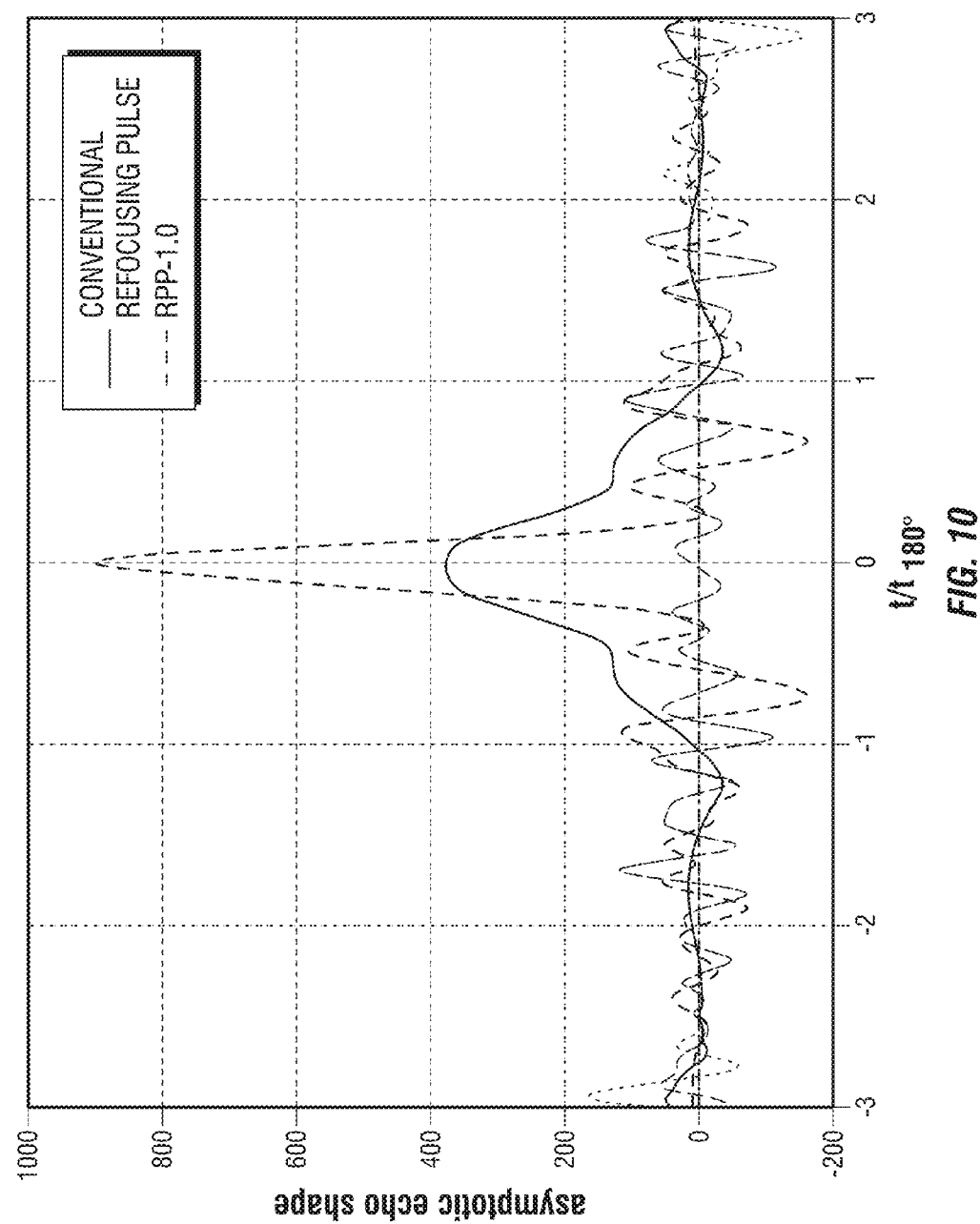
FIG. 10 shows a plot of echo shapes generated by a conventional refocusing pulse and a refocusing pulse in accordance with various embodiments of the disclosure.

The echo shapes of the current implementation and the proposed implementation are shown in FIG. 10. As shown, FIG. 10 illustrates a comparison of the echo shapes generated from 3126 spins in a constant gradient. The lower solid curve shows the echo shape of the conventional refocusing pulse with a rectangular 90-degree pulse and a reduced delay free precession time $T_{180}/\pi$. The top solid curve shows the echo shape of the RPP-1.0 refocusing pulse when combined with one of the novel excitation pulses disclosed herein. The solid curves show in-phase components, while dashed curves show out-of-phase components.

In some embodiments, the RPP pulses outperform the conventional refocusing pulses in a plurality of aspects. These RPP pulses are able to focus spins over a thicker slice and are less sensitive to RF inhomogeneity. As a consequence, in some embodiments, the SNR is doubled when compared with the conventional refocusing pulses, even in the presence of large RF inhomogeneity. In this way, the performance of the RPP pulses greatly exceeds that of conventional pulses. This improved SNR can greatly improve the precision of measurements of porosity, pore size distributions, and other important parameters in petrophysics.

As is also disclosed herein and below, various embodiments of the present invention include combinations of excitation pulses with RPP refocusing pulses.

Excitation Pulses

Various embodiments of the invention are directed to methods for applying an NMR sequence to determine characteristics of a substance within an inhomogeneous static magnetic field. The method includes applying an excitation pulse to the substance within the inhomogeneous static magnetic field to induce a spin effect within the substance. In such an embodiment, the excitation pulse includes a plurality of segments. The method can further include applying a refocusing cycle to the substance, where the refocusing cycle generates a magnetization that is defined by a refocusing axis.

In various embodiments of the present invention, the excitation pulse generates an initial magnetization that is aligned with the refocusing axis of the refocusing pulses. In other words, the excitation pulse generates an initial magnetization that is aligned with a refocusing axis produced by a subsequent refocusing cycle. In contrast, many conventional systems align the initial magnetization with a transverse plane of a molecular nucleus, without regard for the refocusing axis produced by the refocusing pulses.

A "refocusing cycle" in this embodiment, and as described herein, is defined as the duration of the refocusing pulse plus the delay between the refocusing pulse and the next pulse in the sequence.

In various embodiments, application of the excitation pulse is followed by applying RPP refocusing pulses, such as an RPP refocusing pulse that takes the form of: $\alpha_{\phi+\pi}-\beta_\phi-\alpha_{\phi+\pi}$. Furthermore, in some embodiments, following application of the excitation pulse, the method can include performing at least ten refocusing cycles (e.g., 100, 1000 or 5000 refocusing cycles). The refocusing cycles can be performed successively.

Sequences that include such excitation pulses and/or RPP pulses can improve the signal-to-noise ratios (SNR) for NMR processes performed in inhomogeneous field environments. Additionally, as described with respect to the RPP pulses herein, in some cases, the inhomogeneous static magnetic field can vary by a value that is greater than or equal to a nominal amplitude of the refocusing cycle.

In some embodiments, the excitation pulses are specifically designed for a particular series of RPP refocusing pulses (e.g., to further enhance data gathering about a substance in situ). For example, the excitation pulses include a plurality of segments, which in some cases have a substantially constant amplitude "A" as defined herein. The amplitude of the excitation pulses may be chosen to match the amplitude of the RPP refocusing pulses. In various embodiments of the invention, the total excitation pulse duration is at least as long as the echo spacing $T_E$ of the refocusing pulses. For example, in some cases, the excitation pulse can have a total duration equal to or greater than approximately $8\times T_{180}$. Furthermore, in some embodiments, each of the plurality of segments of the excitation pulses include shifted phases (e.g., a phase of 0-degrees or 180 degrees), as described with respect to the RPP pulses. According to various embodiments, the phases are not required to correspond precisely with the stated values (e.g., 0-degrees or 180-degrees). Small modifications to the phase can be made that will still achieve some of the advantages of the invention.

Figure 11:
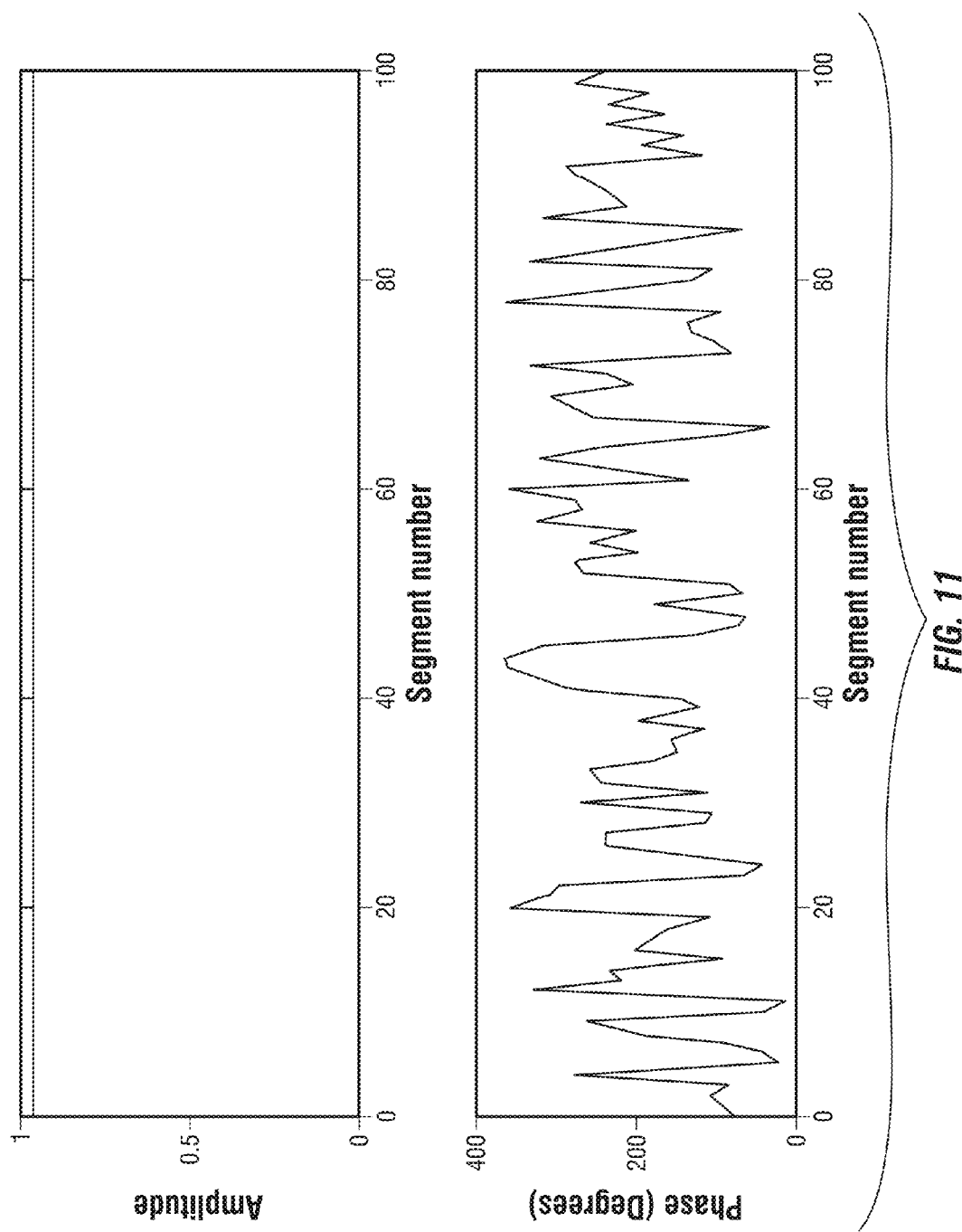
FIG. 11 shows a plot of excitation pulse A in accordance with various embodiments of the disclosure.

FIG. 11 shows a plot of an excitation pulse ("A") according to various embodiments of the invention, where the amplitude and phase of the excitation pulse are plotted as a function of time. In the specific example shown in FIG. 11, the excitation pulse corresponds to an echo spacing of $T_E=6\times T_{180}+T_P$. The excitation pulse includes 100 segments having a length of $0.1\times T_{180}$, resulting in a total length of $10\times T_{180}$. Illustrated embodiments of the invention rely on phase modulation, not amplitude modulation, to improve the SNR ratio in an NMR process. To this end, the excitation pulse has an amplitude that is held constant, while the phase of the excitation pulse is varied from segment to segment. FIG. 12 shows Table 2, which includes phase values (in degrees) for each segment of excitation pulse A, in accordance with various embodiments of the present invention.

FIGS. 13-18 show six more examples of excitation pulses in accordance with various embodiments of the present invention. FIGS. 13-18 show Tables 3-8, which include phase values (in degrees) for each segment of excitation pulses B, C, D, E, F and G, respectively. Each of the segments has a length of $0.1\times T_{180}$. The number of segments from pulse to pulse varies. For example, excitation pulse C includes 202 segments while pulse D includes 156 segments. Accordingly, the total duration of each excitation pulse also varies. The amplitude is held constant between segments in each of the excitation pulse.

Such constant-amplitude excitation pulses are easier to implement in power-constrained hardware when compared to conventional excitation pulses. Also, as is shown and described herein, such constant-amplitude excitation pulses can improve the SNR ratio in an NMR process. FIG. 19 shows Table 9, which compares simulated and measured SNR for various embodiments of the present invention. The first two listed sequences are conventional sequences that use rectangular excitation pulses with 90-degree nutation angles. The first-listed conventional sequence uses refocusing pulses with 180-degree nutation angles, while the second-listed conventional sequence uses refocusing pulses with 135-degree nutation angles. Table 9 also shows the simulated and measured SNR for excitation pulses A-G from FIGS. 11-18. Each excitation pulse is paired with a sequence of RPP-1.0 refocusing pulses. Each listed value of the simulated and measured SNR is normalized to the first-listed conventional sequence. As shown by Table 9, the SNR for each of excitation pulses A-G is significantly greater than the SNR for the two conventional pulse sequences.

Table 9 also shows a theoretical SNR limit for a perfect excitation pulse. Such a perfect excitation pulse aligns every available isochromat along the CPMG refocusing axis. Such a perfect excitation pulse achieves a theoretical upper limit of 3.31. In accordance with one embodiment of the present invention, excitation pulse B achieves an SNR that is approximately 97% of this upper limit. In this manner, illustrative embodiments of the present invention increase SNR over conventional sequences.

Illustrative embodiments of the present invention are also directed to determining characteristics of the excitation pulses, such as an echo shape and an SNR for the excitation pulses. The echo shape characteristics and the SNR can be used to optimize the excitation pulses. For example, characteristics for several different types of excitation pulses can be determined and the excitation pulse with the most desirable characteristics can be selected for use in an NMR tool. A method and process for determining excitation pulse characteristics follows.

Excitation pulses in accordance with various embodiments of the invention are intended to generate an initial magnetization, $M(\Delta\omega_0)$, at time $0^+$ in a substance which is approximately aligned with an effective refocusing axis in a refocusing pulse (e.g., a RPP pulse). This is distinct from the conventional "hard" excitation pulses which generate an initial magnetization on a transverse plane of a molecular nucleus. The inventors have discovered some advantages of the excitation pulse over the conventional hard excitation pulses. For example, excitation pulses can be configured to maximize the amount of asymptotic magnetization. The asymptotic magnetization is given by: $\vec{M}_{asy}=(\vec{M}(0^+)\cdot\hat{n})\hat{n}$, where $\hat{n}$ is the effective axis of the CPMG refocusing cycle, and $M(0^+)$ is the magnetization vector at time $0^+$. Excitation pulses can be configured to maximize the initial dot product, and, as a result, the amount of asymptotic magnetization. The asymptotic echoes actually detected by the coil are produced by the transverse projection of $M_{asy}$ onto the transverse plane, which is given by: $\vec{M}_\perp=(\vec{M}(0^+)\cdot\hat{n})\hat{n}_\perp$, where $\hat{n}_\perp$ is the transverse component of $\hat{n}$. The time domain signals detected for "hard" pulses ($M(0^+)=M_0\hat{x}$) and excitation pulses ($M(0^+)=M_0\hat{n}$) are given by:

$$M_\perp(t) = \int d(\Delta\omega_o)e^{i\Delta\omega_o t}M_\perp(\Delta\omega_o)$$
$$= M_0\int d(\Delta\omega_o)e^{i\Delta\omega_o t}n_\perp^2(\Delta\omega_o), \text{ when } \vec{M}(0^+) = M_0\hat{x}$$
$$= M_0\int d(\Delta\omega_o)e^{i\Delta\omega_o t}n_\perp(\Delta\omega_o), \text{ when } \vec{M}(0^+) = M_0\hat{n}.$$

Excitation pulses generate more signal because $|\vec{n}_\perp|\leq 1$. Thus, illustrative embodiments of the excitation pulses maximize the SNR of the asymptotic echoes for a given refocusing cycle. This cycle is typically repeated many times, and thus determines the peak and average power dissipated and total energy consumed by the sequence. As such, illustrative embodiments of the excitation pulses can serve as a general way to maximize SNR of the CPMG sequence, particularly when subject to power or energy constraints.

It is noteworthy to mention that, because the frequency dependence of $\hat{n}(\Delta\omega_o)$ depends upon the echo spacing $T_E$, some illustrative embodiments of the excitation pulses are specific for a given echo spacing, and a particular type of refocusing pulse (e.g., RPP pulses). In one particular embodiment described herein, the excitation pulses are tailored to the RPP-1.0 pulse shown in FIG. 3(b). For example, FIGS. 11-18 show excitation pulses A-G that are tailored to the RPP-1.0 refocusing pulse.

In various illustrative embodiments, optimizing processes (e.g., OCT) can be used to determine excitation pulses with advantageous SNR and echo characteristics. In some embodiments, the excitation pulses are optimized jointly with refocusing pulses (e.g., both the excitation pulses and refocusing pulses include unconstrained variables). In other embodiments, the excitation pulses and refocusing pulses are optimized separately (e.g., either the excitation pulses or the refocusing pulses include entirely constrained variables).

The optimization can be performed using a uniform distribution of resonance frequency offsets and/or various forms of RF field strength inhomogeneity. Various different cost functions can be used to optimize the excitation and refocusing pulses. In some embodiments, a cost function is used that includes a weighted sum of two properties of an asymptotic echo (e.g., a peak amplitude and a root means squared integral). The root means square integral ensures that SNR is maximized, while the peak amplitude biases the optimization towards echoes with desirable time-domain properties (e.g., localized single peak). In this manner, the cost function is maximized to find the optimum excitation pulse and/or refocusing pulses.

Within the optimization process, certain constraints can be used to find advantageous pulses in accordance with embodiments of the present invention. For example, one constraint may be that the excitation pulse generates an initial magnetization that is aligned with a refocusing axis of a selected series of refocusing pulses. Additional or alternative limitations can also be used. The following is a non-limiting list of potential constraints:

The excitation pulses include at least two segments;
The refocusing pulses include at least two segments;
The excitation pulse modulates phase between segments;
The refocusing pulse modulates phase between segments;
The excitation pulse is at least as long as the echo spacing $T_E$;
The length of the refocusing pulse is less than or equal to $T_{180}$;
The segment length for each segment of the refocusing pulse must be between $0.2\times T_{180}$ and $5\times T_{180}$; and/or
The segment length for each segment of the excitation pulse must be between $0.2\times T_{90}$ and $5\times T_{90}$.

Any or all such constraints can be used to find advantageous pulses in accordance with embodiments of the present invention. Such optimization processes can be used to optimize any of the excitation and refocusing pulses described herein.

Illustrative embodiments of the present invention are also directed to phase cycling techniques that use a phase inversion process. A general RF pulse at frequency $\omega_{RF}$ can be defined as:

$$S(t)=A(t)\cos(\omega_{RF}t+\psi(t)), \qquad (8)$$

where $A(t)$ and $\psi(t)$ are the instantaneous amplitude and phase of the pulse, respectively. In conventional systems, phase cycling of the excitation pulses is performed using conventional phase shifting. In conventional phase shifting, a constant phase $\phi$ is added to the instantaneous phase $-\psi(t)$ of the excitation pulse. The response $\vec{M}^\phi$ of the phase-shifted pulse is simply related to the response $\vec{M}$ of the original pulse by:

$$\vec{M}_\perp^\phi(\Delta\omega_0) = e^{i\phi}\vec{M}_\perp(\Delta\omega_0)$$

$$\vec{M}_z^\phi(\Delta\omega_0) = \vec{M}_z(\Delta\omega_0) \tag{9}$$

According to Equation 9, conventional phase shifting rotates the transverse magnetization by the same amount, and leaves the longitudinal magnetization unaffected.

Conventional CPMG phase-cycling techniques rely on such conventional phase shifting. In such techniques, echoes are acquired in a first scan using a first sequence. Then, the phase of the excitation pulse is shifted by π and the sequence is performed in a second scan. The resultant echoes from the second scan are subtracted from those acquired from the first scan, creating a so-called phase-alternating pair (PAP). The asymptotic magnetization is given by:

$$\vec{M}_{PAP}(\Delta\omega_o) = \hat{n}(\vec{M}(0^+)\cdot\hat{n}) - \hat{n}(\vec{M}^\pi(0^+)\cdot\hat{n}). \tag{10}$$

Here, $\hat{n}$ is the effective refocusing axis, and $\vec{M}(0^+)$ and $\vec{M}^\pi(0^+)$ are the magnetizations produced by the excitation pulse in the first and second scans, respectively. Equation (9) predicts that the phase shift inverts the transverse, but not the longitudinal component of the initial magnetization, which is reflected as:

$$\vec{M}_\perp^\pi(0^+) = -\vec{M}_\perp(0^+)$$

$$M_z^\pi(0^+) = +M_z(0^+). \tag{11}$$

The phase cycling cancels the longitudinal portion of the initial magnetization, and the asymptotic magnetization is given by:

$$\vec{M}_{PAP}(\Delta\omega_o) = 2\hat{n}(\vec{M}_\perp(0^+)\cdot\hat{n}_\perp), \tag{12}$$

where $\hat{n} = \hat{n}_z + \hat{n}_\perp$. The projection of $M_{PAP}(\Delta\omega_0)$ onto the transverse plane is detected by the coil. In some cases, for excitation pulses according to various embodiments of the invention, conventional phase cycling may not be optimal because only the overlap of the transverse components of $M(\Delta\omega_0)$ with $\hat{n}$ is retained in the asymptotic magnetization after phase cycling.

Instead of conventional phase cycling, illustrative embodiments of the present invention use a phase inversion process. Refocusing cycles act as composite rotations, which include refocusing pulses and segments of free precession, during which $\hat{n}_1 = \hat{z}_1$. In some embodiments, RPP refocusing pulses contain segments with phases of 0 and π, and so have rotation axes $\hat{n}_2$ that are confined to the $\hat{x}$-$\hat{z}$ plane. Also, in some cases, refocusing cycles are symmetric, which causes the refocusing axis (axis of the composite rotation) to lie in the plane spanned by $\hat{n}_1$ and $\hat{n}_2$, e.g., the $\hat{x}$-$\hat{z}$ plane. It is beneficial to retain both the $\hat{x}$ and the $\hat{z}$ components of the magnetization produced by the excitation pulse. To this end, illustrative embodiments of the present invention use a phase cycling technique that includes a phase inversion process (e.g., replacing $\psi(t)$ with $-\psi(t)$).

In various embodiments, the phase inversion process can be applied as follows. In accordance with a specific embodiment of the invention, echoes are acquired in a first scan using a first sequence including an excitation pulse and a series of refocusing pulses. The phase of the excitation pulse is inverted (e.g., its complex conjugate is formed) and the sequence is run again in a second scan using the inverted excitation pulse and the series of refocusing pluses. In some embodiments, the second scan is performed before the first scan. The resultant echoes from the second scan are subtracted from those acquired during the first scan. The asymptotic magnetization is given by:

$$\vec{M}_{PI}(\Delta\omega_o) = \vec{n}(\vec{M}(0^+)\cdot\vec{n}) - \vec{n}(\vec{M}^{-\psi}(0^+)\cdot\vec{n}). \tag{13}$$

where $\vec{M}^{-\psi(t)}(\Delta\omega_0)$ is the magnetization produced by the phase-inverted excitation pulse. The $\hat{x}$ and $\hat{z}$ components of the magnetization produced by the phase-inverted excitation pulse are related in a simple way to those produced by the original pulse. In this manner, the following relationships are determined:

$$M_x^{-\psi}(0^+;\Delta\omega_o) = -M_x(0^+;-\Delta\omega_o)$$

$$M_z^{-\psi}(0^+;\Delta\omega_o) = +M_z(0^+;-\Delta\omega_o). \tag{14}$$

The $\hat{x}$ component of the refocusing axis is symmetric about $\Delta\omega_0 = 0$, while the $\hat{z}$ component is anti-symmetric. In this manner, the following relationships are determined:

$$n_x(\Delta\omega_0) = n_x(-\Delta\omega_0)$$

$$n_z(\Delta\omega_0) = -n_z(-\Delta\omega_0). \tag{15}$$

In certain embodiments of the invention, the excitation pulses produce magnetization that matches the refocusing axis, so for some pulses, the same symmetry relationships apply:

$$M_x(0^+;\Delta\omega_o) \approx M_x(0^+;-\Delta\omega_o)$$

$$M_z(0^+;\Delta\omega_o) \approx -M_z(0^+;-\Delta\omega_o). \tag{16}$$

Within this approximation, equations (14) and (16) can be used to show that the asymptotic magnetization after the phase inversion process is:

$$\vec{M}_{PI}(\Delta\omega_o) = \vec{n}[(M_x(0^+;\Delta\omega_o) - M_x^{-\psi}(0^+;\Delta\omega_o))n_x + \tag{17}$$
$$(M_z(0^+;\Delta\omega_o) - M_z^{-\psi}(0^+;\Delta\omega_o))n_z]$$
$$= \vec{n}[(M_x(0^+;\Delta\omega_o) + M_x(0^+;-\Delta\omega_o))n_x +$$
$$(M_z(0^+;\Delta\omega_o) - M_z(0^+;-\Delta\omega_o))n_z]$$
$$\approx 2\vec{n}[M_x(0^+;\Delta\omega_o)n_x + M_z(0^+;\Delta\omega_o)n_z]$$

In some embodiments of the present invention, the phase inversion process retains both the $\hat{x}$ and $\hat{z}$ components of the magnetization produced by the excitation pulses, which results in greater asymptotic signal as compared with conventional phase cycling.

The phase inversion process can also be applied (e.g., instead of phase shifting) to various other excitation pulses described herein. The excitation pulse can even be used with rectangular π/2 excitation pulses. Doing so, in many cases, is not advantageous because rectangular π/2 excitation pulses produce longitudinal magnetization that is symmetric about $\Delta\omega_0 = 0$, i.e., $M_z(0^+; -\Delta\omega_0)$. In such cases, phase inversion will cancel out the ẑ component, as shown by equation (17).

Figure 20A:
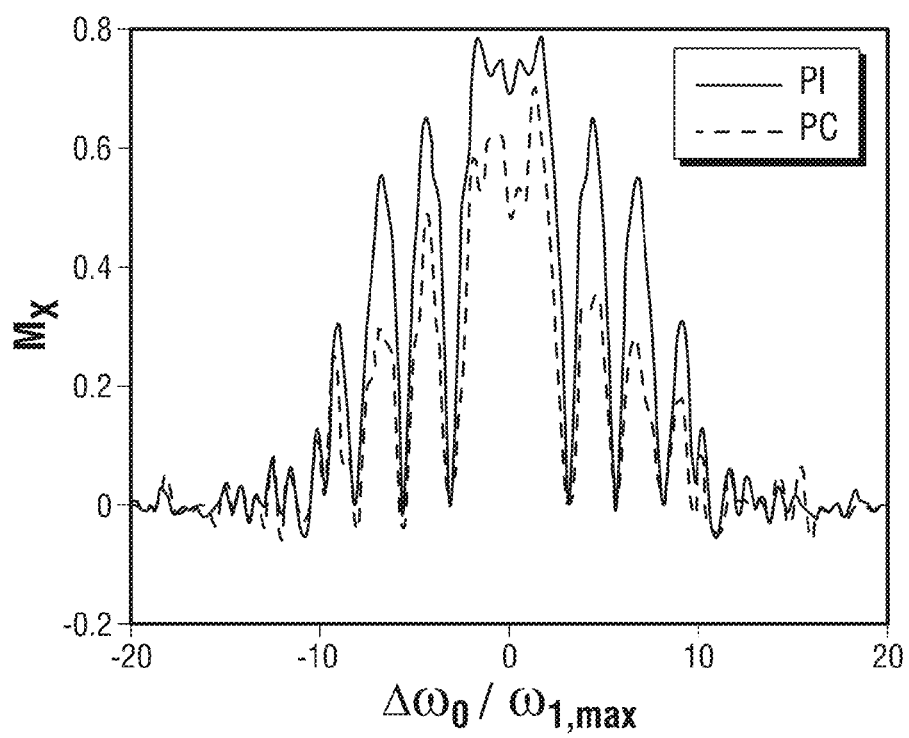
FIG. 20 shows a plot of an asymptotic magnetization signal and a plot of a time-domain echo signal, generated in accordance with various embodiments of the present disclosure.
Figure 20B:
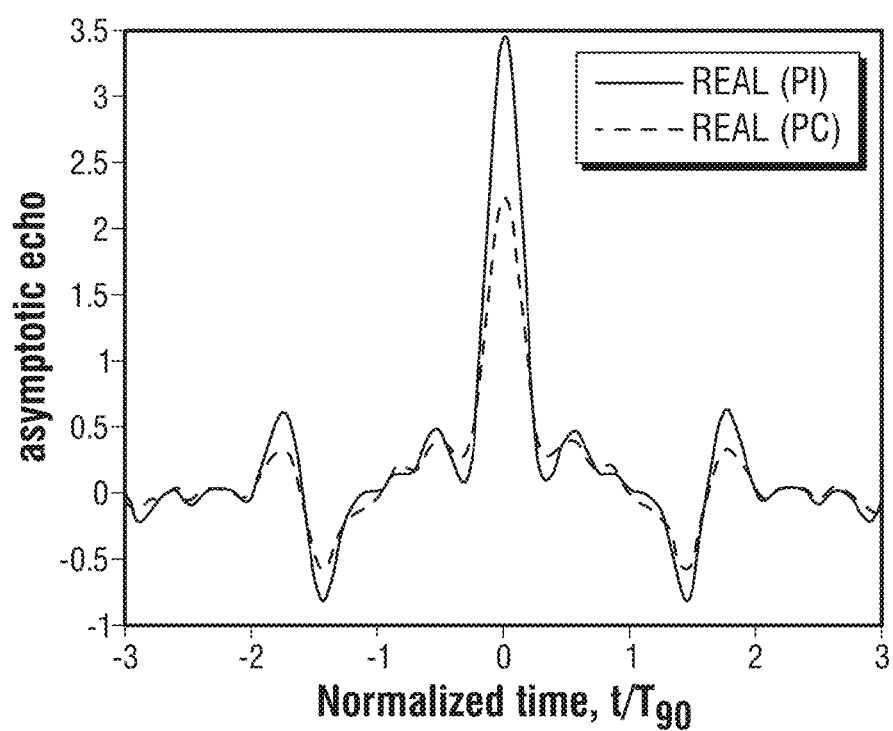

FIG. 20 shows plots of an asymptotic magnetization signal and a time-domain echo signal in accordance with various embodiments of the present invention. The top plot shows asymptotic magnetization signals produced by a phase inversion process and a conventional phase shifting process (e.g., shifting the phase by π). The pulse sequence used for each case includes excitation pulse A, as shown in FIGS. 11 and 12, and a series of RPP-1.0 refocusing pulses, as shown in FIG. 3. The bottom plot shows time-domain echo signals produced by the phase inversion process and the conventional phase shifting process. As can be seen from the plot, the phase inversion process produces a significantly larger signal in each case.

The excitation pulses and/or the phase inversion processes performed in accordance with various embodiment of the present invention can significantly improve SNR for NMR processes performed in inhomogeneous field environments. In some cases, various embodiments of the present invention include SNRs (in power units) are 3.2 times higher than conventional sequences. As a result, the time required to obtain a given SNR is reduced by a similar factor.

Additional or Alternative Excitation Pulses

In yet another embodiment of the present invention, a method for applying an NMR sequence includes applying an excitation pulse to a substance within an inhomogeneous static magnetic field, followed by applying a series of refocusing pulses to the substance. The excitation pulse is applied to induce a spin effect within the substance, as in conventional approaches. In contrast to conventional approaches, various embodiments of the invention include applying an excitation pulse having a plurality of segments with a substantially constant amplitude, where each of the segments has one phase selected from no more than two distinct phases. As described herein, this embodiment allows for application of excitation and refocusing pulses using NMR equipment which may lack capability to switch between many different phases. Thus, illustrative embodiments of the present invention advantageously allow for application of the pulses described herein using existing NMR hardware, without the need for retrofitting or upgrading of hardware.

In various embodiments of the present invention, an excitation pulses has N segments. The RF amplitude and phase is constant within each of the segments, but can vary across segments. The length of the n-th segment is $T_n$. In some embodiments, for the purposes of simplifying hardware implementations, all segments can have the same RF amplitude. In these cases, this constant RF amplitude can be approximately equal to that of the refocusing pulses (e.g., the selected RPP pulses).

Additionally, various embodiments of these excitation pulses modulate the RF phases of each of the segments between two distinct phases: (a) approximately $\phi+\pi/2$; and (b) approximately $\phi+3\pi/2$, where $\phi$ is the phase for a series of subsequent refocusing pulses. In further illustrative embodiments, the excitation pulses include segments with alternate phases that differ by $\pi$ and the segments include an arbitrary phase shift $\phi_0$ relative to the refocusing pulses. In further specific embodiments, the arbitrary phase shift $\phi_0$ is a multiple of $\pi/2$. In yet further illustrative embodiments, the segments do not include an arbitrary phase shift (e.g., $\phi_0=0$). In various embodiments, such phase modulation between segments provides improved echo characteristics. Furthermore, according to various embodiments, the phases are not required to correspond precisely with the stated phases (e.g., $\pi$, $\pi/2$, $\phi+\pi/2$, or $\phi+3\pi/2$). Small modifications to the phase can be made that will still achieve some of the advantages of the invention.

In certain embodiments of the present invention, the excitation pulses are composed of a plurality of segments (e.g., 10, 20, 100 or 200 segments). Additionally, in some embodiments, the excitation pulse can have a duration greater than or equal to approximately nine times $T_{180}$. These examples should not be construed as limiting the scope of the invention.

In some cases, application of such an excitation pulse is followed by applying refocusing pulses as described herein, such as an RPP refocusing pulse that takes the form of: $\alpha_{\phi+\pi}-\beta_\phi-\alpha_{\phi+\pi}$. In one particular embodiment, RPP-1.0 refocusing pulses are applied in refocusing cycles following application of the excitation pulse. In this case, as described with respect to the RPP pulses above, each refocusing pulse in the cycle can include an initial segment $\alpha$ and a final segment $\alpha$, each having equal durations. Each RPP pulse can further include a middle segment $\beta$ having a duration distinct from the initial segment and final segment. The initial segment, middle segment and final segment have a substantially constant amplitude. Furthermore, the phase of the middle segment is shifted 180 degrees with respect to each of the initial segment and the final segment.

In various embodiments, following application of the excitation pulse, the method can include performing at least ten refocusing cycles (e.g., 100, 1000 or 5000 refocusing cycles). The refocusing cycles can be performed successively, and each can last for approximately the duration of the refocusing pulse plus the delay between the refocusing pulse and the next pulse (e.g., the next refocusing pulse) in the sequence.

Figures 22, 23:
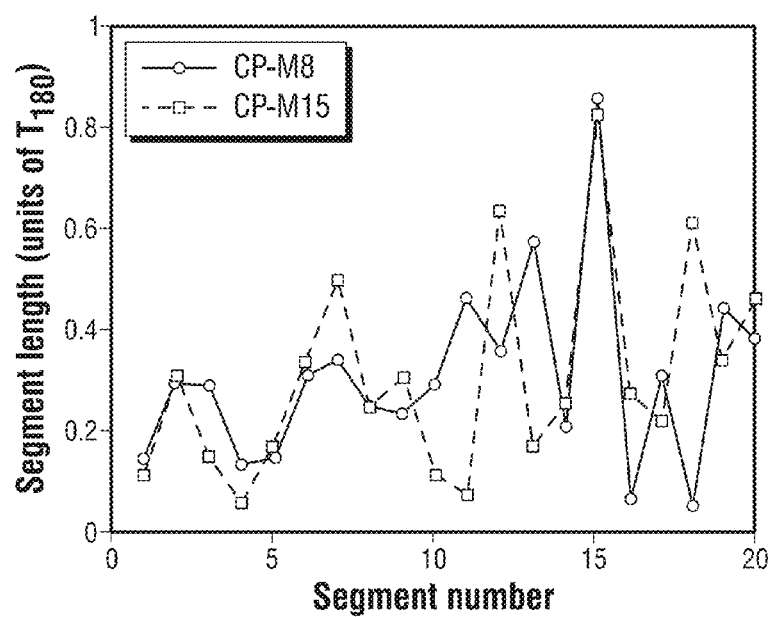
FIG. 22 shows Table 11, which includes echo characteristics generated by the excitation pulses defined in FIG. 21.
FIG. 23 shows a plot of segment number by segment length for excitation pulses in accordance with various embodiments of the disclosure.

Tables 10 and 11 in FIGS. 21 and 22 show excitation pulses in accordance with various embodiments of the present invention. Table 10 (FIG. 21) illustrates the segment lengths of several excitation pulses in accordance with various embodiments of the present invention: CP-M8, CP-M10, CP-M12, and CP-M15. All segment lengths in Table 2 are normalized to the length of a rectangular 90-degree pulse at the same RF power level. With the exception of CP-M12, which has 10 segments, each excitation pulse has 20 segments. The total pulse lengths are listed at the bottom of Table 10. The excitation pulses are optimized for use with an RPP-1.0 refocusing pulse. The excitation pulses include segment phases that alternate between $\phi+\pi/2$ and $\phi+3\pi/2$, while the RPP-1.0 segment phases alternate between $\phi$ and $\phi+\pi$.

Table 11 (FIG. 22) shows a summary of values of a squared echo integral produced by the excitation pulses described in Table 10 (FIG. 21). In order to create this table, the excitation pulses were used in CPMG sequences, and the squared integral of the asymptotic echo was calculated. That squared integral of the asymptotic echo was then normalized to the default case of rectangular excitation and refocusing pulses at the same RF power level. Additionally, the half-power bandwidth of the echoes was calculated and included in Table 11. As shown, the CP-M8 and CP-M15 excitation pulses achieved the best performance.

FIG. 23 illustrates a graphical representation of segment number plotted by segment length for the CP-M8 and CP-M15 excitation pulses, respectively. The CP-M8 and CP-M15 excitation pulses have very similar segment lengths and total lengths (e.g., $12.33 \times T_{90}$ and $12.39 \times T_{90}$, respectively).

Figure 24:
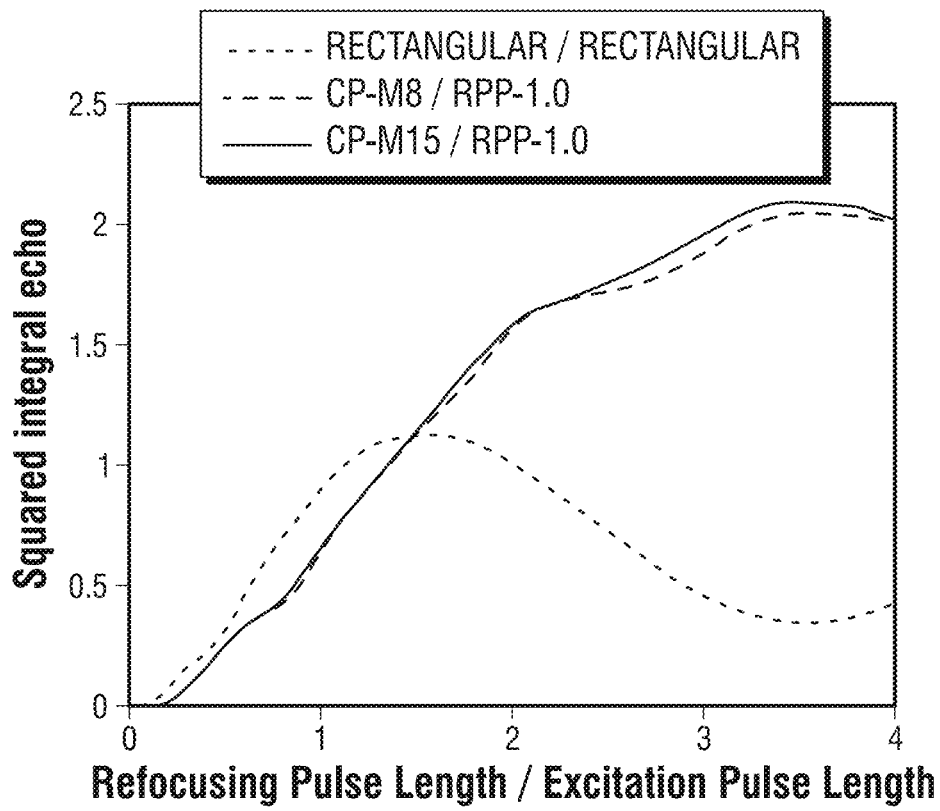
FIG. 24 shows a plot of a squared echo integral for a conventional refocusing pulse and for a plurality of refocusing pulses in accordance with various embodiments of the disclosure.

FIG. 24 shows a plot of a squared echo integral for a conventional refocusing pulse and for a plurality of refocusing pulses in accordance with various embodiments of the invention. The squared echo integral is plotted as a function of a ratio of refocusing pulse length to excitation pulse length (e.g., refocusing pulse length/excitation pulse length). In this plot, the excitation and refocusing pulses are assumed to have the same RF power level and the excitation pulse length is fixed, while the length of the refocusing pulse is varied. Additionally, the results have been normalized to those obtained with rectangular pulses at a ratio of 2 (e.g., $T_{180}/T_{90}$).

In FIG. 24, a "stretched" or "squeezed" version of the RPP-1.0 pulse was used. In other words, the segment lengths were modified in proportion to the total pulse length. The plot shows that the maximum signal energy for rectangular pulses occurs at approximately a ratio of 1.5, and is about 12% higher than the default case at a ratio of 2. This behavior explains why NMR well logging tools often use a ratio of approximately 1.5. The plot also shows that the signal energy for the RPP and the CP-M pulses increases monotonically with pulse length for the ratio is less than 3 (e.g., between 2 and 3), before saturating at a maximum value.

As explained above, illustrative embodiments of the present invention are also directed to optimizing excitation pulses using optimizing processes. Optimizing processes (e.g., OCT) can be used to determine excitation pulses with advantageous SNR and echo characteristics. In various embodiments, desirable excitation pulses are determined by maximizing the asymptotic CPMG echoes produced by excitation pulses and refocusing pulses. To this end, various constraints can be used to find advantageous pulses in accordance with embodiments of the present invention. In one example, the segments of the excitation pulse are constrained so that they modulate between two distinct phases: (a) $\phi+\pi/2$; and (b) $\phi+3\pi/2$. As explained above, in various embodiments, this form of phase modulation between segments provides improved echo characteristics.

In another example, the excitation pulse length can be restricted to a particular number of segments (e.g., no greater than 100 segments). As a practical matter, the use of a large number of segments may not be desirable because optimizing the pulses becomes much harder as the number of search dimensions increases.

In yet another example, the amplitude of the segments of the excitation pulses is constrained so that it is constant within the pulse. This configuration simplifies hardware implementation and limits peak power consumption.

In a further example, the excitation pulse segment lengths are constrained to a particular range. In various embodiments of the invention, excitation pulse segment lengths are the single optimization variables (e.g., all other variables are fixed).

The following is a non-limiting list of additional potential constraints for the optimization process:

All segments of the excitation pulse have a constant amplitude;
The amplitude of the excitation pulse is equal to the amplitude of the refocusing pulses;
The excitation pulse has a constant phase within pulse segments;
The excitation pulse modulates phase between segments;
The excitation pulse is at least as long as the echo spacing $T_E$;
The segments of the excitation pulse module between phases having a multiple of $\pi/2$;
The segments of the excitation pulse module between no more than two phases;
The segments of the excitation pulse modulate between two distinct phases: (a) $\phi+\pi/2$; and (b) $\phi+3\pi/2$; and/or
The excitation pulse is no longer than $100 \times T_{90}$.

Any or all such constraints can be used to find advantageous pulses in accordance with embodiments of the present invention.

An NMR process (including CPMG sequencing) according to embodiments of the present invention may include detecting NMR signals from the substance during application of the series of refocusing pulses, such that applying the refocusing pulses allows for data gathering about properties of the substance in the inhomogeneous static magnetic field. In particular, detecting the NMR signals from the substance allows for determination of one or more characteristics of the substance in situ. Determination of these characteristics is enhanced by use of one or more of the excitation pulses and refocusing pulses in accordance with embodiments of the present invention.

Figure 25:
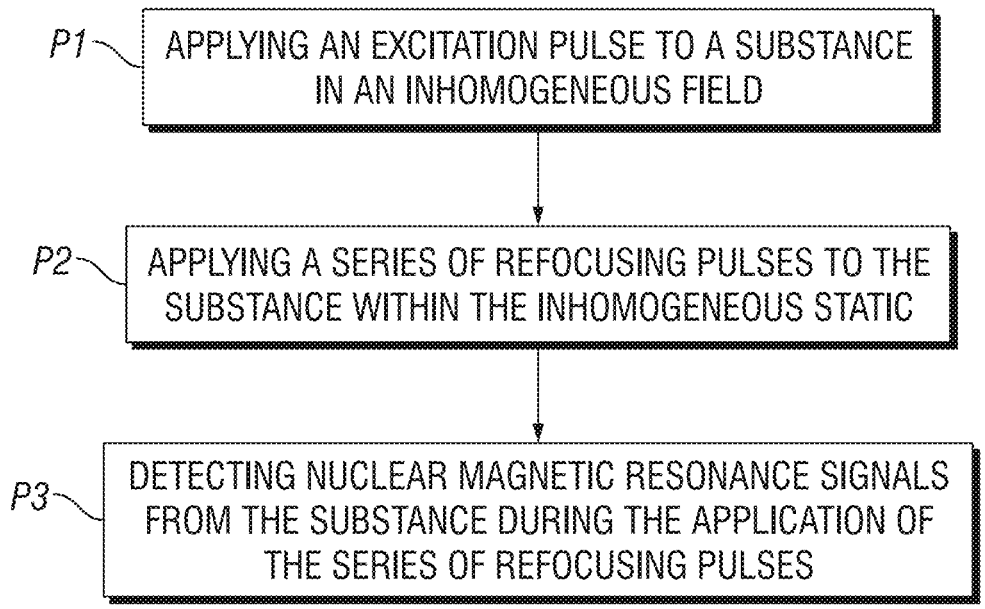
FIG. 25 shows a flow diagram illustrating processes in a method in accordance with various embodiments of the disclosure.

FIG. 25 shows a flow diagram illustrating processes in a method according to various embodiments of the invention. As described with respect to various aspects of the invention, a method can include the following processes:

Process P1: Applying an excitation pulse to a substance in an inhomogeneous magnetic field. The excitation pulse can take the form of any excitation pulse described with respect to the embodiments of the invention. In some cases, the excitation pulse generates an initial magnetization aligned with a refocusing axis to be produced by a refocusing cycle performed after the excitation pulse. In various embodiments, the excitation pulse includes a plurality of segments, where each of the segments has a substantially constant amplitude and each of the segments has one phase selected from no more than two distinct phases.

Process P2: Following application of the excitation pulse, process P2 can include applying a series of refocusing pulses to the substance within the inhomogeneous magnetic field. The series of refocusing pulses can take the form of any refocusing pulses described with respect to the embodiments of the invention, and can include, for example, one or more of the RPP pulses described herein.

Process P3: Concurrently with or following application of the series of refocusing pulses, process P3 can include detecting NMR signals from the substance within the inhomogeneous field. These NMR signals can be subsequently analyzed according to conventional methods.

It is understood that processes P1, P2, P3 and/or any other processes described herein according to the various aspects of the invention can be implemented utilizing one or more computing devices. In one embodiment discussed further herein, an aspect of the invention includes a computing device configured to perform one or more of the herein-noted processes. In still another embodiment, a computer-readable medium is disclosed including program code having instructions for performing one or more of the herein-noted processes when executed on a computing device.

Figure 26:
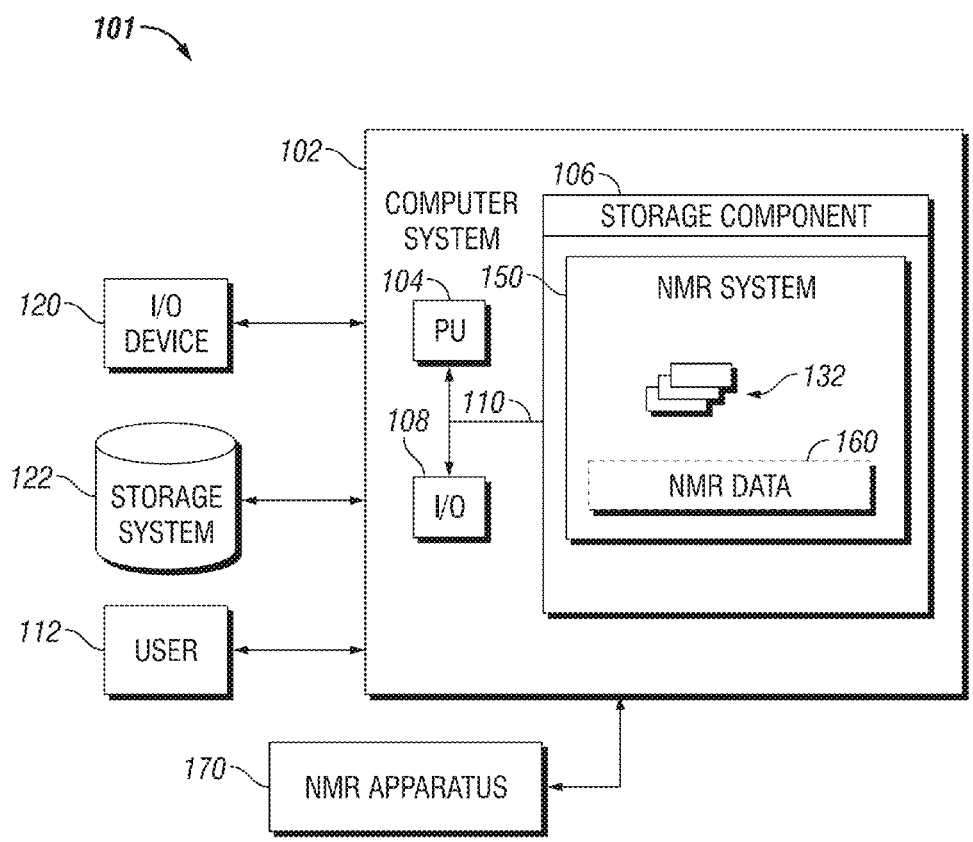
FIG. 26 shows an illustrative environment for performing NMR processes in accordance with various embodiments of the disclosure.

FIG. 26 depicts an illustrative environment 101 for performing the NMR processes described herein with respect to various embodiments. To this extent, the environment 101 includes a computer system 102 that can perform one or more processes described herein in order to determine characteristics of a substance, e.g., within an inhomogeneous static magnetic field. In particular, the computer system 102 is shown as including an NMR system 150, which makes computer system 102 operable to determine characteristics of a substance by performing any/all of the processes described herein and implementing any/all of the embodiments described herein.

The computer system 102 is shown including a processing component 104 (e.g., one or more processors), a storage component 106 (e.g., a storage hierarchy), an in-put/output (I/O) component 108 (e.g., one or more I/O interfaces and/or devices), and a communications pathway 110. In general, the processing component 104 executes pro-gram code, such as the NMR system 150, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O de-vices, which enable a user 112 to interact with the computer system 102 and/or one or more communications devices to enable a system user 112 to communicate with the computer system 102 using any type of communications link. To this extent, the NMR system 150 can manage a set of interfaces (e.g., graphical user interface (s), application program interface, etc.) that enable human and/or system users 112 to interact with the NMR system 150. Further, the NMR system 150 can manage (e.g., store, retrieve, create, manipulate, organize, present, etc.) data, such as NMR data 160 (including NMR signal data) using any solution. The NMR system 150 can also communicate with a conventional external input/output (I/O) device 120 and/or a conventional external storage system 122 to read/write data (e.g., NMR data 160). The NMR system 150 can additionally communicate with an NMR apparatus 170, which can include any conventional NMR hardware and/or software capable of generating a static magnetic field, providing pulses according to instructions from the NMR system 150, obtaining NMR signal data, etc.

In any event, the computer system 102 can comprise one or more general purpose computing articles of manufacture (e.g., computing devices) capable of executing program code, such as the NMR system 150, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the NMR system 150 can be embodied as any combination of system software and/or application software.

Further, the NMR system 150 can be implemented using a set of modules 132. In this case, a module 132 can enable the computer system 102 to perform a set of tasks used by the NMR system 150, and can be separately developed and/or implemented apart from other portions of the NMR system 150. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of NMR system 150 fixed thereon (e.g., one or more modules 132). However, it is understood that the computer system 102 and NMR system 150 are only representative of various possible equivalent computer systems that may perform a process described herein. To this extent, in other embodiments, the functionality provided by the computer system 102 and NMR system 150 can be at least partially implemented by one or more computing devices that include any combination of general and/or specific purpose hardware with or without program code. In each embodiment, the hardware and program code, if included, can be created using conventional engineering and programming techniques, respectively.

Regardless, when the computer system 102 includes multiple computing devices, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide data, such as NMR data 160 using a variety of different solutions. The computer system 102 can generate NMR data 160, from one or more data stores, receive NMR data 160, from another system such as an NMR apparatus 170, the external I/O device 120 and/or the external storage system 122, send NMR data 160 to another system, etc.

While shown and described herein as a method and system for determining characteristics of substances, it is understood that aspects of the invention further provide various alternative embodiments. For example, in one embodiment, the invention provides a computer program fixed in at least one computer-readable medium, which when executed, enables a computer system to determine characteristics of substances. To this extent, the computer-readable medium includes program code, such as the NMR system 150 (FIG. 26), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the NMR system 150 (FIG. 26), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for determining characteristics of substances. In this case, a computer system, such as the computer system 102 (FIG. 26), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

The invention has been described with reference to particular embodiments, but variations within the spirit and scope of the invention will occur to those skilled in the art. For example, it will be understood that other suitable pulse sequences can be employed. Also, it will be understood that the techniques described herein according to embodiments can be used in combination with other measurements and techniques, including but not limited to, measurement of relaxation rates, spectroscopy, diffusion constant and other pulse field gradient measurements. Furthermore, the process for determining optimal refocusing and excitation pulses described herein extends to other cases (e.g., joint optimization of both the excitation and refocusing pulses in an arbitrary distribution of resonance frequencies and RF field strengths).

We claim:

1. A method for applying a nuclear magnetic resonance (NMR) sequence, the method comprising:
   applying an excitation pulse to a substance within an inhomogeneous static magnetic field to induce a spin effect within the substance, wherein the excitation pulse includes a plurality of segments; and
   applying a refocusing cycle to the substance, wherein the refocusing cycle generates a magnetization that is aligned with an effective refocusing axis;
   wherein the refocusing cycle includes at least one refocusing pulse that includes an initial segment, a middle segment and a final segment,
   wherein the initial segment and the final segment each have substantially equal durations,
   wherein the middle segment has a duration,
   wherein each of the initial segment, the middle segment, and the final segment has a substantially constant amplitude,
   wherein a phase of the middle segment is shifted approximately 180 degrees with respect to a phase of each of the initial segment and the final segment, and
   wherein the excitation pulse generates an initial magnetization that is aligned with the effective refocusing axis.

2. The method of claim 1, wherein each of the plurality of segments of the excitation pulse has a substantially constant amplitude.

3. The method of claim 1, wherein the plurality of segments of the excitation pulse modulate between phases that are a multiple of $\pi/2$.

4. The method of claim 1, wherein the excitation pulse has a duration that is greater than or equal to approximately eight times T180.

5. The method of claim 1, wherein the excitation pulse has a duration greater than or equal to an echo spacing.

6. The method of claim 1, wherein the inhomogeneous static magnetic field varies by a value that is greater than or equal to a nominal amplitude of the refocusing cycle.

7. The method of claim 1, further comprising:
   performing at least 10 refocusing cycles after the applying of the excitation pulse.

8. The method of claim 1, further comprising:
   applying a second excitation pulse to the substance within the inhomogeneous static magnetic field to induce a spin effect within the substance; and
   applying the refocusing cycle to the substance;
   wherein the second excitation pulse includes an inverted phase with respect to the first excitation pulse.

9. The method of claim 1, further comprising:
   detecting nuclear magnetic resonance signals from the substance during the application of the series of refocusing pulses.

10. A method for applying a nuclear magnetic resonance (NMR) sequence, the method comprising:
    applying an excitation pulse to a substance within an inhomogeneous static magnetic field to induce a spin effect within the substance, wherein the excitation pulse includes a plurality of segments, wherein each segment of the excitation pulse has a substantially constant amplitude with a phase shift between adjacent segments, and wherein each segment of the excitation pulse has one phase selected from no more than two distinct phases; and
    applying a series of refocusing pulses to the substance within the inhomogeneous static magnetic field after the applying of the excitation pulse the series of refocusing pulses having an effective refocusing axis,
    wherein the refocusing cycle includes at least one refocusing pulse that includes an initial segment, a middle segment and a final segment,
    wherein the initial segment and the final segment each have substantially equal durations,
    wherein the middle segment has a duration,
    wherein each of the initial segment, the middle segment, and the final segment has a substantially constant amplitude,
    wherein a phase of the middle segment is shifted approximately 180 degrees with respect to a phase of each of the initial segment and the final segment, and
    wherein the excitation pulse generates an initial magnetization that is aligned with the effective refocusing axis.

11. The method of claim 10, wherein the inhomogeneous static magnetic field varies by a value approximately greater than or equal to a nominal amplitude of the series of refocusing pulses.

12. The method of claim 10, wherein the excitation pulse includes at least 10 segments.

13. The method of claim 10, wherein the excitation pulse has a duration greater than or equal to approximately nine times T180.

14. The method of claim 10, wherein the two distinct phases are:
    (a) approximately $\phi+90$ degrees; and
    (b) approximately $\phi+270$ degrees,
    wherein $\phi$ is a phase for the series of refocusing pulses.

15. The method of claim 10, further comprising:
    detecting nuclear magnetic resonance signals from the substance during the application of the series of refocusing pulses.

16. The method of claim 1, wherein plurality of segments of the excitation pulse have a phase shift between adjacent segments.

17. The method of claim 16, wherein the plurality of segments of the excitation pulse modulate between two distinct phases.

18. The method of claim 16, wherein:
the refocusing cycle includes at least one refocusing pulse having a phase $\phi$; and
the plurality of segments of the excitation pulse modulate between two distinct phases of approximately $\phi+90$ degrees and approximately $\phi+270$ degrees.

\* \* \* \* \*